(12) United States Patent
Liu

(10) Patent No.: US 12,414,542 B2
(45) Date of Patent: Sep. 16, 2025

(54) DRYING MACHINE

(71) Applicant: SHENZHEN QIANHAI HOMERUN SMART TECHNOLOGY CO., LTD., Shenzhen (CN)

(72) Inventor: Kun Liu, Shenzhen (CN)

(73) Assignee: SHENZHEN QIANHAI HOMERUN SMART TECHNOLOGY CO., LTD., Guangdong (CN)

( * ) Notice: Subject to any disclaimer, the term of this patent is extended or adjusted under 35 U.S.C. 154(b) by 174 days.

(21) Appl. No.: 18/014,179

(22) PCT Filed: Sep. 18, 2021

(86) PCT No.: PCT/CN2021/119365
§ 371 (c)(1),
(2) Date: Jan. 3, 2023

(87) PCT Pub. No.: WO2022/057926
PCT Pub. Date: Mar. 24, 2022

(65) Prior Publication Data
US 2023/0255180 A1   Aug. 17, 2023

(30) Foreign Application Priority Data

Sep. 21, 2020  (CN) .......................... 202010992640.0
Sep. 21, 2020  (CN) .......................... 202010992806.9
(Continued)

(51) Int. Cl.
*A01K 13/00*   (2006.01)

(52) U.S. Cl.
CPC ................................ *A01K 13/001* (2013.01)

(58) Field of Classification Search
CPC ................................................ A01K 13/001
(Continued)

(56) References Cited

U.S. PATENT DOCUMENTS 1,714,635 A * 5/1929 Schafer .................... A61D 7/00
                                                       119/678
3,175,534 A * 3/1965 Pollard ................ A01K 13/001
                                                       219/400
(Continued)

FOREIGN PATENT DOCUMENTS

CN          2159656 Y      3/1994
CN        203412818 U      1/2014
(Continued)

OTHER PUBLICATIONS

Merged translation of FR-2550054-A1 (Year: 1985).*
(Continued)

*Primary Examiner* — Morgan T Jordan
(74) *Attorney, Agent, or Firm* — Schwegman Lundberg & Woessner, P.A.

(57) ABSTRACT

A drying machine, comprising a box body. A first partition plate is provided in the box body, and the first partition plate is located in front of a rear wall of the box body; a drying cavity and a first accommodation cavity are respectively located on two sides of the first partition plate; the first accommodation cavity is defined between the first partition plate and the rear wall; a fan wheel is provided in the first accommodation cavity, and a rotation axis of the fan wheel is perpendicular to the first partition plate and the rear wall; a first air inlet is formed in the first partition plate, a second air inlet is formed in the rear wall; the first air inlet and the second air inlet are respectively opposite to the axial direction of the fan wheel; the fan wheel realize the inner circulation and outer circulation of air.

20 Claims, 21 Drawing Sheets

(30) Foreign Application Priority Data

Sep. 21, 2020 (CN) .......................... 202022070191.2
Sep. 21, 2020 (CN) .......................... 202022086090.4
Sep. 21, 2020 (CN) .......................... 202022087091.0

(58) Field of Classification Search
USPC .......................................... 34/509, 511, 535
See application file for complete search history.

(56) References Cited

U.S. PATENT DOCUMENTS

| | | | | |
|---|---|---|---|---|
| 3,884,191 | A * | 5/1975 | Stout | A01K 13/001 119/671 |
| 3,962,994 | A * | 6/1976 | Petrucciani | A01K 1/034 119/484 |
| 3,985,102 | A * | 10/1976 | Yonezawa | A01K 13/001 219/400 |
| 4,183,323 | A * | 1/1980 | Maines | A01K 13/001 119/416 |
| 4,314,410 | A * | 2/1982 | Nichols | A01K 13/001 34/233 |
| 4,505,229 | A * | 3/1985 | Altissimo | A01K 13/001 119/668 |
| 4,559,903 | A * | 12/1985 | Bloom | A01K 13/001 219/400 |
| 4,947,799 | A * | 8/1990 | Parker | A01K 13/001 34/619 |
| 5,025,572 | A * | 6/1991 | Cordier | A01K 13/001 34/201 |
| 5,035,728 | A * | 7/1991 | Fang | B03C 3/68 422/120 |
| 5,368,816 | A * | 11/1994 | Detzer | F24F 8/26 422/4 |
| 5,435,269 | A * | 7/1995 | Chen | A01K 13/001 119/668 |
| 5,761,915 | A * | 6/1998 | Rao | F24F 3/1423 62/271 |
| 6,058,886 | A * | 5/2000 | Haines | A01K 13/001 119/606 |
| 6,276,304 | B1 * | 8/2001 | Tai | A01M 13/003 119/448 |
| 6,318,295 | B1 * | 11/2001 | Wade | A01K 1/033 119/500 |
| 6,826,850 | B2 * | 12/2004 | Jewell | A01K 13/001 34/232 |
| 7,997,234 | B1 * | 8/2011 | Hughey | A01K 1/0245 119/500 |
| 8,186,307 | B2 * | 5/2012 | Moharram | A01K 13/001 119/671 |
| 8,757,096 | B2 | 6/2014 | Doumas | |
| D897,613 | S * | 9/2020 | Bae | D30/108 |
| 2007/0006815 | A1 * | 1/2007 | Correa | A01K 31/007 119/443 |
| 2007/0245975 | A1 * | 10/2007 | Udelle | A01K 13/004 119/600 |
| 2008/0053379 | A1 * | 3/2008 | Markewitz | A01K 13/00 119/600 |
| 2008/0060586 | A1 * | 3/2008 | Lewis, Jr. | A01K 1/0047 119/500 |
| 2010/0071224 | A1 | 3/2010 | Chung | |
| 2011/0061601 | A1 * | 3/2011 | Correa | A01K 1/0047 119/448 |
| 2012/0055414 | A1 * | 3/2012 | Correa | A01K 31/04 119/448 |
| 2013/0055962 | A1 * | 3/2013 | Scoggins | A01K 13/001 119/453 |
| 2015/0366163 | A1 * | 12/2015 | Carter | A01K 13/001 119/678 |
| 2019/0021272 | A1 * | 1/2019 | Marshall, III | F24F 8/10 |
| 2020/0029530 | A1 * | 1/2020 | Yoon | F26B 21/00 |
| 2020/0305389 | A1 * | 10/2020 | Meng | A01K 13/001 |
| 2021/0000075 | A1 * | 1/2021 | Im | A47K 10/48 |
| 2022/0000065 | A1 * | 1/2022 | Bender | A01K 1/011 |
| 2023/0225285 | A1 * | 7/2023 | Levin | A01K 1/0245 119/500 |

FOREIGN PATENT DOCUMENTS

| | | | | |
|---|---|---|---|---|
| CN | 107950424 | A * | 4/2018 | |
| CN | 207574278 | | 7/2018 | |
| CN | 207948496 | U | 10/2018 | |
| CN | 208175742 | U * | 12/2018 | |
| CN | 109673531 | A | 4/2019 | |
| CN | 208692005 | U | 4/2019 | |
| CN | 110063265 | A | 7/2019 | |
| CN | 209153276 | U | 7/2019 | |
| CN | 110461144 | A | 11/2019 | |
| CN | 209711094 | U | 12/2019 | |
| CN | 209788157 | U | 12/2019 | |
| CN | 209824796 | U | 12/2019 | |
| CN | 210959914 | U | 7/2020 | |
| CN | 211185398 | U | 8/2020 | |
| CN | 111869588 | A | 11/2020 | |
| CN | 111990280 | A | 11/2020 | |
| CN | 112005899 | A | 12/2020 | |
| CN | 213784776 | U | 7/2021 | |
| CN | 113557980 | A * | 10/2021 | |
| FR | 2550054 | A1 * | 2/1985 | |
| FR | 2580467 | A * | 10/1986 | A01K 13/00 |
| JP | 2001324176 | A | 11/2001 | |
| JP | 4278633 | B2 | 3/2009 | |
| JP | 2020520681 | A | 7/2020 | |
| KR | 20080068977 | A | 7/2008 | |
| KR | 20150142807 | | 12/2015 | |
| KR | 20160011469 | A | 2/2016 | |
| KR | 101606267 | B1 | 3/2016 | |
| KR | 101840655 | | 3/2018 | |
| KR | 20180044684 | A | 5/2018 | |
| KR | 20180046454 | | 5/2018 | |
| KR | 20190111445 | A | 10/2019 | |
| KR | 102137572 | B1 | 7/2020 | |
| WO | 2022057926 | | 3/2022 | |
| WO | WO-2022119443 | A1 * | 6/2022 | A01K 67/033 |

OTHER PUBLICATIONS

Merged translation of FR-2580467-A (Year: 1986).*
Merged translation of CN-107950424-A (Year: 2018).*
Merged translation of CN-208175742-U (Year: 2018).*
Merged translation of WO-2022119443-A1 (Year: 2022).*
Merged translation of CN 113557980 A (Year: 2021).*
"International Application Serial No. PCT CN2021 119365, Written Opinion mailed Dec. 17, 2021", 9 pgs.
"International Application Serial No. PCT CN2021 119365, International Search Report mailed Dec. 17, 2021", 7 pgs.
"International Application Serial No. PCT CN2021 119365, International Preliminary Report on Patentability mailed Mar. 30, 2023", 12 pgs.
"Korean Application No. 10-2022-7045776, Office Action dated Feb. 12, 2025", w English Translation, (Feb. 12, 2025), 18 pgs.
"Chinese Application Serial No. 202022086083.4, Decision on Examination of Invalidity Declaration Request dated Sep. 2, 2022", w/ English Translation, (Sep. 2, 2022), 16 pgs.
"Chinese Application Serial No. 202022086083.4, Decision on Examination of Invalidity Declaration Request dated Sep. 5, 2023", w/ English Translation, (Sep. 5, 2023), 21 pgs.
"Chinese Application Serial No. 202122284917.7, Decision on Examination of Invalidity Declaration Request dated Jan. 6, 2025", w/ English Translation, (Jan. 6, 2025), 19 pgs.
"Chinese Application Serial No. 202180005061.5, Decision on Examination of Invalidity Declaration Request dated Mar. 5, 2025", w/ English Translation, (Mar. 5, 2025), 29 pgs.
"Chinese Application Serial No. 202180005061.5, Office Action dated Feb. 11, 2023", w/ English Translation, (Feb. 11, 2023), 15 pgs.

(56) References Cited

OTHER PUBLICATIONS

"Chinese Application Serial No. 202180005061.5, Office Action dated Oct. 7, 2023", w/ English Translation, (Oct. 7, 2023), 17 pgs.
"Japanese Application No. 2023-503503, Office Action dated Jan. 23, 2024", w/ English Translation, (Jan. 23, 2024), 8 pgs.

* cited by examiner

DRYING MACHINE

CROSS REFERENCES TO THE RELATED APPLICATIONS

The application is a national stage entry of PCT/CN2021/119365 filed on Sep. 18, 2021, which claims priority to Chinese patent applications No. 202010992640.0 filed on Sep. 21, 2020, 202010992806.9 filed on Sep. 21, 2020, 202022070191.2 filed on Sep. 21, 2020, 202022086090.4 filed on Sep. 21, 2020, and 202022087091.0 filed on Sep. 21, 2020, the entire contents of which are incorporated herein by reference.

TECHNICAL FIELD

The present disclosure relates to the technical field of drying apparatuses, and in particular to a drying machine.

BACKGROUND

A pet drying box is an apparatus for drying the fur of a pet after the pet is bathed and groomed. In the related art, most of pet drying boxes are made by assembling simple fan wheels and heating assemblies, so that the pet drying boxes have no reasonable air channel design, resulting in poor drying effects and large noise and affecting the comfort of pets in the pet drying boxes. Alternatively, the fan wheel of the pet drying box is arranged at the top or bottom of the pet drying box, wherein the arrangement of the fan wheel at the top of the pet drying box provides a longer air channel and causes a great loss of wind energy and low drying efficiency, and the arrangement of the fan wheel at the bottom of the pet drying box may result in liquid leakage which causes a safety risk of the pet drying box.

SUMMARY

The present disclosure aims to solve at least one of the technical problems existing in the prior art. For this purpose, an object of the present disclosure is to provide a drying machine which increases its air supply rate, reduces the loss of wind energy, improves its drying efficiency, reduces noise during its operation, and has a reduced production cost.

The drying machine according to an embodiment of the present disclosure comprises: a box body, wherein a first partition plate is provided in the box body, and the first partition plate is located in front of a rear wall of the box body; a drying cavity and a first accommodation cavity are respectively located on two sides of the first partition plate; the first accommodation cavity is defined between the first partition plate and the rear wall; a fan wheel is provided in the first accommodation cavity, and a rotation axis of the fan wheel is perpendicular to the first partition plate and the rear wall; a first air inlet is formed in the first partition plate, a second air inlet is formed in the rear wall, and the first air inlet and the second air inlet each are axially opposite to the fan wheel; when the fan wheel rotates, an airflow inside the drying cavity is suitable for entering the first accommodation cavity through the first air inlet under the action of the fan wheel and then flowing into the drying cavity, and the airflow outside the drying machine is suitable for entering the first accommodation cavity through the second air inlet under the action of the fan wheel and then flowing into the drying cavity, so as to realize the inner circulation and the outer circulation of air by means of one fan wheel.

According to the drying machine, such as the pet drying machine of the embodiment of the present disclosure, the interior of the box body is divided into the drying cavity and the first accommodation cavity by locating the first partition plate in front of the rear wall of the box body, the first accommodation cavity is defined between the first partition plate and the rear wall of the box body, the fan wheel is provided in the first accommodation cavity, the first air inlet is formed in the first partition plate, the second air inlet is formed in the rear wall, and the first air inlet and the second air inlet each are axially opposite to the fan wheel. Thus, the air supply rate of the drying machine is increased, the loss of wind energy is reduced, the drying efficiency of the drying machine is improved, the nonuniformity of the hot and cold air in the box body caused by an additional fan wheel can also be avoided, and the noise during the operation of the drying machine and the production cost of the drying machine can be reduced.

According to some embodiments of the present disclosure, a fan wheel housing is provided between the first partition plate and the rear wall, the fan wheel is arranged in the fan wheel housing, and an air channel is defined between the fan wheel and the fan wheel housing, and when the fan wheel rotates, the airflow in the drying cavity sequentially flows through the first air inlet and the air channel and then flows into the drying cavity, and the airflow outside the drying machine sequentially flows through the second air inlet and the air channel and then flows into the drying cavity.

According to some embodiments of the present disclosure, a second partition plate is provided in the box body, a second accommodation cavity in direct communication with an air channel outlet of the air channel is defined between the second partition plate and an inner wall of the box body at a position in the fan wheel housing corresponding to the air channel outlet, an air outlet is formed in the second partition plate, and the drying cavity is located above the second partition plate; and when the fan wheel operates to rotate, the airflow inside the drying cavity is suitable for sequentially flowing through the first air inlet, the air channel, the second accommodation cavity and flowing into the drying cavity through the air outlet, and the airflow outside the drying machine is suitable for sequentially flowing through the second air inlet, the air channel, the second accommodation cavity and flowing into the drying cavity through the air outlet.

According to some embodiments of the present disclosure, the second partition plate is removably arranged in a lower portion of the box body.

According to some embodiments of the present disclosure, the air outlet comprises a plurality of air outlet orifices; and the second partition plate comprises: a partition plate body; and two partition plate sections, wherein the two partition plate sections are respectively arranged on the left side and the right side of the partition plate body, the two partition plate sections extend obliquely upwards from bottom to top in a direction away from the center of the partition plate body, and a plurality of air outlet orifices are formed in both the two partition plate sections and the partition plate body.

According to some embodiments of the present disclosure, each partition plate section is an arc-shaped partition plate projecting away from the partition plate body. According to some embodiments of the present disclosure, a heating assembly is provided at an air outlet of the spiral air channel.

According to some embodiments of the present disclosure, a negative ion generator is provided on the first partition plate, and an output end of the negative ion generator extends into the first accommodation cavity; and an ozone disinfection apparatus is provided on the heating assembly.

According to some embodiments of the present disclosure, the air channel is a spiral air channel.

According to some embodiments of the present disclosure, a projection of at least a portion of the fan wheel housing on the first partition plate is in the form of a spiral.

According to some embodiments of the present disclosure, a projection of at least the portion of the fan wheel housing on the first partition plate is in the form of an Archimedean spiral.

According to some embodiments of the present disclosure, the air channel has an air channel outlet, and the cross-sectional area of at least a portion of the air channel gradually increases toward the air channel outlet in a circumferential direction of the fan wheel.

According to some embodiments of the present disclosure, the fan wheel housing is arranged on at least one of the first partition plate and the rear wall.

According to some embodiments of the present disclosure, the drying box further comprises an electric motor support; and the fan wheel housing comprises: a first fan wheel housing arranged on the first partition plate; and a second fan wheel housing arranged on the electric motor support, the second fan wheel housing and the first fan wheel housing jointly defining a fan wheel accommodation cavity for accommodating the fan wheel.

According to some embodiments of the present disclosure, the electric motor support is formed with an air inlet hole that runs therethrough in an axial direction of the fan wheel, the electric motor support is in sealed connection with the rear wall on a peripheral side of the air inlet hole, and outside air sucked by the fan wheel sequentially passes through the second air inlet and the air inlet hole and enters the fan wheel accommodation cavity.

According to some embodiments of the present disclosure, the electric motor support is detachably connected to the first partition plate.

According to some embodiments of the present disclosure, an electric motor is provided in the fan wheel accommodation cavity, an output shaft of the electric motor is fixed to the fan wheel, and the electric motor is mounted on the second fan wheel housing.

According to some embodiments of the present disclosure, a rear surface of the first partition plate extends backwards from the first fan wheel housing.

According to some embodiments of the present disclosure, the fan wheel is a forward-inclined fan wheel.

According to some embodiments of the present disclosure, the fan wheel is provided as an axially through fan wheel.

According to some embodiments of the present disclosure, a wall forming the drying cavity is formed with at least one through ventilation hole.

According to some embodiments of the present disclosure, at least one cat stroking opening is formed in the box body, and a cat stroking door is provided at the cat stroking opening for opening or closing the cat stroking opening.

According to some embodiments of the present disclosure, an opening is formed in the box body, a removable viewing window is provided at the opening, and the cat stroking opening is formed in the viewing window.

According to some embodiments of the present disclosure, one end of the cat stroking door is pivotably connected to the viewing window by means of a pivoting assembly; and a locking assembly is provided between the other end of the cat stroking door and the viewing window, the cat stroking door is adapted for opening the cat stroking opening when the locking assembly is unlocked, and the cat stroking door is fixed to the viewing window when the other end of the cat stroking door is locked by the locking assembly.

According to some embodiments of the present disclosure, a placement slot is formed in the box body, a fragrance box is removably arranged in the placement slot by means of a magnetic attraction assembly, the fragrance box has a first configuration and a second configuration in the placement slot, at least one through hole is formed in the fragrance box, the interior of the fragrance box is not in communication with the interior of the box body when the fragrance box is in the first configuration, and the interior of the fragrance box is in communication with the interior of the box body through the through hole when the fragrance box is in the second configuration.

Some of additional aspects and advantages of the present disclosure will be given in the following description, and will be apparent from the following description, or may be learned by practice of the present disclosure.

BRIEF DESCRIPTION OF THE DRAWINGS

The foregoing and/or additional aspects and advantages of the present disclosure will become apparent and easily understood from the following description of the embodiments taken in conjunction with the accompanying drawings, in which.

LIST OF REFERENCE NUMERALS

Figure 1:
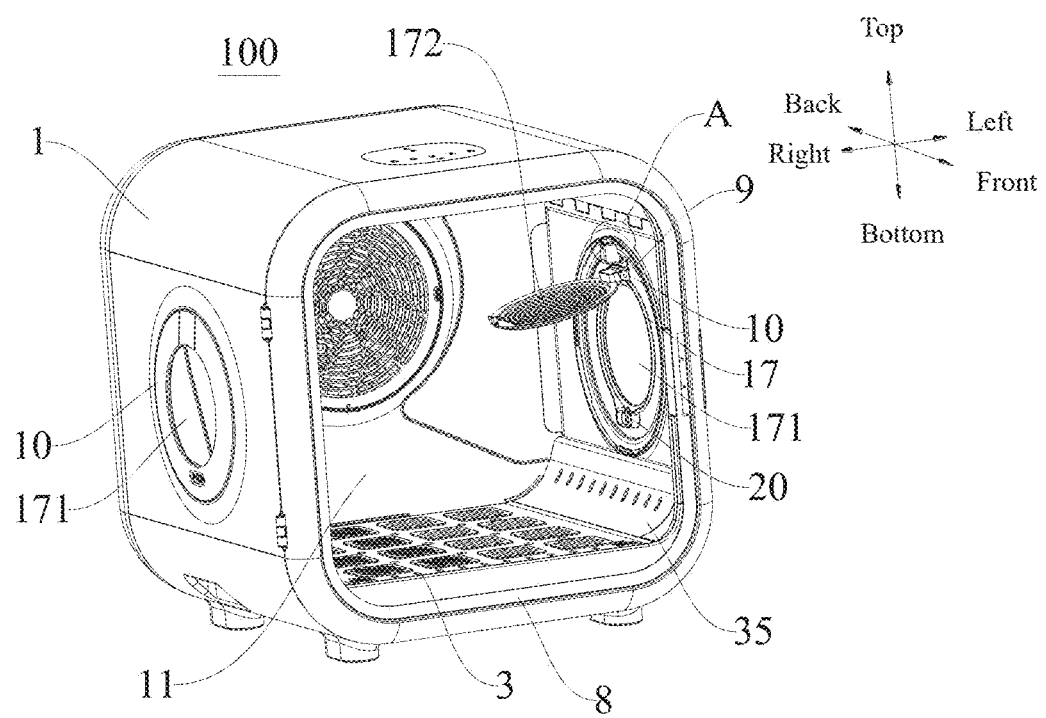
FIG. 1 is a schematic diagram of a drying machine according to an embodiment of the present disclosure.

100: Drying machine;
1: Box body; 11: Drying cavity; 12: First accommodation cavity; 13: Rear wall; 131: Second air inlet;
14: Second accommodation cavity; 15: Extension; 151: First concave surface; 16: Dust filter screen;
17: Opening; 171: Cat stroking opening; 1711: Avoidance opening; 1712: Ventilation hole;
172: Cat stroking door; 173: Snap-fitting section; 1731: First stopping protrusion; 174: Snap-fitting groove;
175: Mounting opening; 18: Limiting groove; 19: Placement slot; 21: Fan wheel;
22: Electric motor; 23: Fan wheel housing; 231: Air channel; 2311: Air channel outlet;
232: First partition plate; 2321: First air inlet; 2322: First fan wheel housing; 233: Electric motor support;
2331: Second fan wheel housing; 3: Second partition plate; 31: Air outlet; 311: First air outlet orifice;
312: Second air outlet orifice; 32: Groove; 33: Mounting hole; 34: Partition plate body;
341: Boss; 35: Partition plate section; 4: Snap-fitting assembly; 41: Fastener; 411: Snap portion;
412: Limiting protrusion; 413: Penetrating hole; 414: Second concave surface; 42: Slot; 5: Supporting member;
6: Mounting assembly; 61: Sliding entrance; 62: First mounting recess; 621: First rib;
622: Second rib; 7: First limiting block; 8: Door body; 9: Pivoting assembly;
91: First mounting portion; 911: Mounting lug; 92: Second mounting portion;
93: Pivot shaft; 94: Torsion spring; 10: Viewing window; 101: Flange section; 102: Second stopping protrusion;
103: Second limiting block; 20: Locking assembly; 201: Locking slot; 202: Locking member; 203: Locking protrusion;
2031: Bulge; 30: Barrier plate; 301: Second mounting recess; 40: Fragrance box; 401: Shell;
4011: Third mounting recess; 4012: Protrusion; 4013: Shell side wall; 4014: Matching groove;
4015: Through hole; 4016: Third rib; 402: Cover; 4021: Cover side wall;
4022: Matching protrusion; 50: Magnetic attraction assembly; 501: Screw; 502: Magnetic member;
60: Seal; 70: Upper housing; 701: First mounting cavity; 702: Second mounting cavity;
80: Heating assembly; 90: Electrical control element.

DETAILED DESCRIPTION OF THE EMBODIMENTS

The embodiments of the present disclosure will be described below in detail, examples of which are illustrated in the accompanying drawings, wherein like or similar reference numerals refer to the same or similar elements or elements having the same or similar functions throughout the description. The embodiments described below with reference to accompanying drawings are exemplary and are intended to be illustrative of the present disclosure, and will not be interpreted as limiting the present disclosure.

In the description, it should be understood that the orientation or positional relationships indicated by the terms "center", "upper", "lower", "front", "rear", "left", "right", "vertical", "horizontal", "top", "bottom", "inner", "outer", etc. are based on the orientation or positional relationship shown in the accompanying drawings and are only for facilitating the description of the embodiments of the present disclosure and simplifying the description, rather than indicating or implying that a device or an element referred to must have a particular orientation or be constructed and operated in a particular orientation, and therefore will not be interpreted as limiting the embodiments of the present disclosure.

It should be noted that the terms "first" and "second" are used for descriptive purposes only, and cannot be construed as indicating or implying relative importance or implicitly indicating the number of technical features indicated. Thus, the features defined with "first" and "second" can explicitly or implicitly include one or more of the features. Further, in the description of the present disclosure, the term "a plurality of" means two or more, unless otherwise specified.

A drying machine 100 according to an embodiment of the present disclosure will be described below with reference to FIGS. 1-30. The drying machine 100 may be, but is not limited to, a pet drying machine. In the description of the present application, a pet drying machine is taken as an example to illustrate the drying machine 100.

As shown in FIGS. 1-30, the drying machine 100 according to the embodiment of the present disclosure comprises a box body 1.

Specifically, a first partition plate 232 is provided in the box body 1, the first partition plate 232 is located in front of a rear wall 13 of the box body 1, and a drying cavity 11 and a first accommodation cavity 12 are respectively located on two sides of the first partition plate 232; the first accommodation cavity 12 is defined between the first partition plate 232 and the rear wall 13, a fan wheel 21 is provided in the first accommodation cavity 12, and a rotation axis of the fan wheel 21 is perpendicular to the first partition plate 232 and the rear wall 13; a first air inlet 2321 is formed in the first partition plate 232, a second air inlet 131 is formed in the rear wall 13, and the first air inlet 2321 and the second air inlet 131 each are axially opposite to the fan wheel 21.

When the fan wheel 21 rotates, an airflow inside the drying cavity 11 is suitable for entering the first accommodation cavity 12 through the first air inlet 2321 under the action of the fan wheel 21 and then flowing into the drying cavity 11, and an airflow outside the drying machine 100 is suitable for entering the first accommodation cavity 12 through the second air inlet 13 under the action of the fan wheel 21 and then flowing into the drying cavity 11, so as to realize inner circulation and outer circulation of air by means of one fan wheel 21.

For example, in the examples shown in FIGS. 1, 4, 5 and 7, the box body 1 may be a square box body, the fan wheel 21 is provided in an upper portion of the first accommodation cavity 12, and the first air inlet 2321 and the second air inlet 13 each are axially opposite to the fan wheel 21. When a pet is dried in the drying machine 100, the fan wheel 21 rotates, the airflow in the drying cavity 11 in this case may axially enter the fan wheel 21 through the first air inlet 2321, and meanwhile, the airflow outside the drying machine 100 such as the pet drying machine can axially enter the fan wheel 21 through the second air inlet 131, and the airflow in the fan wheel 21 can be then expelled to the first accommodation cavity 12 in a radial direction of the fan wheel 21 and be compressed in the first accommodation cavity 12, and finally flows into the drying cavity 11 under the action of the fan wheel 21 to dry the pet. Thus, compared with a conventional pet drying box, the present application can simultaneously realize the inner circulation and outer circulation of air by means of one fan wheel 21, replenish fresh air, and make the pet more safe; also, the supply air rate of the drying machine 100 is increased, the loss of wind energy is reduced, and accordingly the drying efficiency of the drying machine 100 can be improved. In addition, with one fan wheel 21, it is possible to avoid the nonuniformity of hot and cold air in the box body 1 caused by an additional fan wheel 21, and it is also possible to effectively reduce noise sources, which reduces the noise during operation of the drying machine 100 and reduces the production cost of the drying machine 100.

Providing the fan wheel 21 in the first accommodation cavity 12 between the rear wall 13 of the box body 1 and the first partition plate 232 allows the fan wheel 21 to smoothly introduce the airflow outside the drying machine 100 when rotating, so as to achieve the exchange of air inside and outside the drying machine 100, it is possible to prevent liquid leakage at a bottom wall of the box body 1 which causes a potential safety hazard to the fan wheel 21, the use safety of the drying machine 100 is improved, and accordingly the service life of the drying machine 100 can be ensured.

According to the drying machine 100, such as the pet drying machine, of the embodiment of the present disclosure, the interior of the box body 1 is divided into the drying cavity 11 and the first accommodation cavity 12 by locating the first partition plate 232 in front of the rear wall 13 of the box body 1, the first accommodation cavity 12 is defined between the first partition plate 232 and the rear wall 13 of the box body 1, the fan wheel 21 is provided in the first accommodation cavity 12, the first air inlet 2321 is formed in the first partition plate 232, the second air inlet 131 is formed in the rear wall 13, and the first air inlet 2321 and the second air inlet 131 each are axially opposite to the fan wheel 21. Thus, the air supply rate of the drying machine 100 is increased, the loss of wind energy is reduced, the drying efficiency of the drying machine 100 is improved, the nonuniformity of the hot and cold air in the box body 1 caused by an additional fan wheel 21 can also be avoided, and the noise during the operation of the drying machine 100 and the production cost of the drying machine 100 can be reduced.

Figure 13:
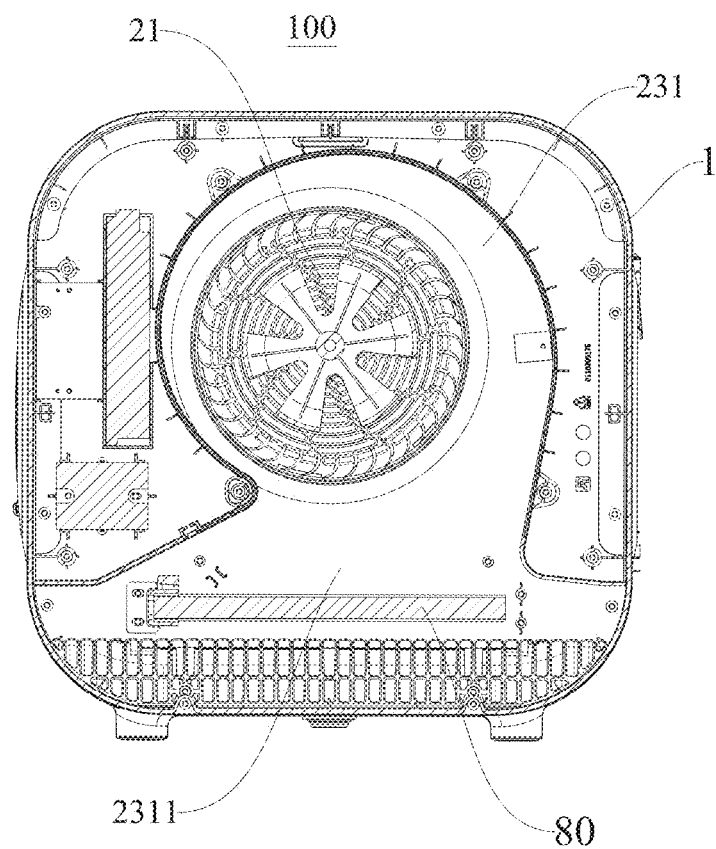
FIG. 13 is a cross-sectional view of the drying machine at another view angle according to an embodiment of the present disclosure.
Figure 14:
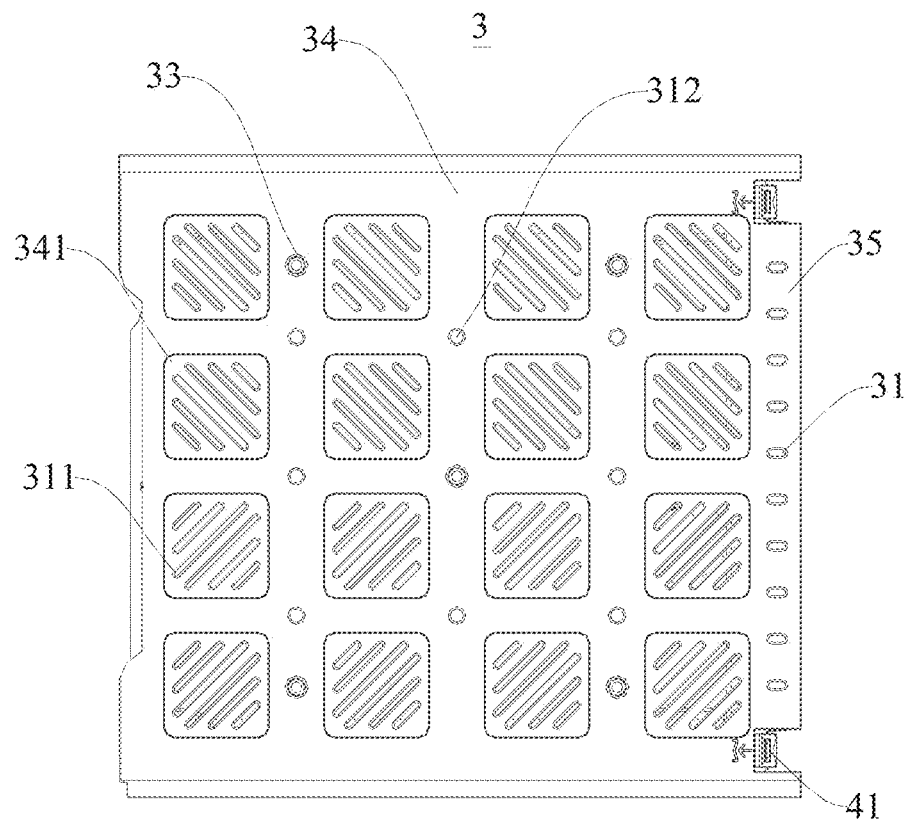
FIG. 14 is a top view of a second partition plate of the drying machine according to an embodiment of the present disclosure.

According to some embodiments of the present disclosure, as shown in FIG. 13, a fan wheel housing 23 is provided between the first partition plate 232 and the rear wall 13, the fan wheel 21 is arranged in the fan wheel housing 23, and an air outlet channel 231 is defined between the fan wheel 21 and the fan wheel housing 23; when the fan wheel 21 rotates, the airflow inside the drying cavity 11 sequentially flows through the first air inlet 2321 and the air channel 231 and then flows into the drying cavity 11, and the airflow outside the drying machine 100 sequentially flows through the second air inlet 131 and the air channel 231 and then flows into the drying cavity 11. When the fan wheel 21 rotates, the fan wheel 21 can radially expel the airflow flowing toward the fan wheel 21 into the air outlet channel 231 and compress the airflow in the air outlet channel 231, and the compressed airflow can flow toward the drying cavity 11 under the guiding effect of the air outlet channel 231. As a result, it is possible to avoid the loss of air supply rate while allowing the airflow flowing toward the fan wheel 21 to flow into the drying cavity 11 as much as possible, so that the drying efficiency of the drying machine 100 can be improved.

According to some embodiments of the present disclosure, with reference to FIGS. 1, 3, 5 and 7, a second partition plate 3 is provided in the box body 1, a second accommodation cavity 14 in direct communication with an air channel outlet 2311 of the air channel 231 is defined between the second partition plate 3 and an inner wall of the box body 1 at a position in the fan wheel housing 23 corresponding to the air channel outlet 2311, an air outlet 31 is formed in the second partition plate 3, and the drying cavity 11 is located above the second partition plate 3; and when the fan wheel 21 operates to rotate, the airflow inside the drying cavity 11 is suitable for sequentially flowing through the first air inlet 2321, the air channel 231 and the second accommodation cavity 14 and flowing into the drying cavity 11 through the air outlet 31, and the airflow outside the drying machine 100 is suitable for sequentially flowing through the second air inlet 131, the air channel 231 and the second accommodation cavity 14 and flowing into the drying cavity 11 through the air outlet 31. Thus, the airflow flowing from the air channel outlet 2311 can directly flow toward the second accommodation cavity 14, so that the drying efficiency can be improved. Furthermore, when the pet is lying on the second partition plate 3, the airflow inside the second accommodation cavity 14 can flow to the pet position through the air outlet 31 so as to dry the pet, and the airflow for drying in this case can be blown to the abdomen of the pet, shortening the action time of the drying process while improving the ventilation effect of the box body 1, further improving the drying efficiency, and ensuring the drying effect. Also, the second partition plate 3 can allow the water or impurities on the pet to flow onto the bottom wall of the box body 1 through the air outlet 31 under the effect of gravity, ensuring the cleanliness of the drying cavity 11 of the box body 1.

Further, referring to FIGS. 11-17 in combination with FIG. 1, the second partition plate 3 is removably arranged in a lower portion of the inside of the box body 1 to facilitate the separation of the second partition plate 3 from the box body 1, thereby facilitating the cleaning of the bottom wall of the box body 1 and the second partition plate 3, preventing the accumulation of water and messy environment in the box body 1 to provide clean drying environment, which in turn improves the comfort of the pet during drying. Moreover, after the second partition plate 3 is damaged, the second partition plate 3 can be dismounted from the box body 1 so as to replace the second partition plate 3 with a new one, and the second partition plate is easy to dismount and can prolong the service life of the drying machine 100.

Still further, the second partition plate 3 is detachably connected to the box body 1 by means of at least one snap-fitting assembly 4, so as to facilitate the detachable fit between the second partition plate 3 and the box body 1, meanwhile, the difficulty in mounting and dismounting the second partition plate 3 can be reduced, and the efficiency of dismounting and dismounting can be improved. In such an arrangement, a user can easily dismount the second partition plate 3 so as to clean the bottom wall of the box body 1, thereby improving the user experience. Of course, in other embodiments, the detachable connection between the second partition plate 3 and the box body 1 can also be implemented by means of hole-post fitting, insertion fitting, etc., which will not be limited herein.

The snap-fitting assembly 4 comprises a snap fastener 41 and a slot 42, a groove 32 is provided on the second partition plate 3, the snap fastener 41 is arranged on an inner wall of the groove 32, and the snap fastener 41 has a snap portion 411. An extension 15 extending toward the snap fastener 41 is provided on the box body 1, the slot 42 is defined between the extension 15 and the inner wall of the groove 32, and the snap portion 411 is fitted in the slot 42. As shown in FIGS. 11-17, an opening of the groove 32 may be open into the box body 1 so as to fit with the slot 42 formed in the box body 1. The slot 42 may be defined between the extension 15 and a bottom wall of the groove 32. Thus, by means of the fit between the space defined by the extension 15 and the groove 32 and the snap portion 411, the snap-fit connection between the second partition plate 3 and the box body 1 is implemented, so that the user can easily dismount the second partition plate 3 to clean the bottom of the box body 1, facilitating cleaning and replacement, further improving the comfort of the pet during drying, and improving the user experience. Optionally, the snap fastener 41 and the inner wall of the groove 32 may be formed as one piece, so that the structural reliability of the snap fastener 41 can be enhanced.

In some optional embodiments, the cross section of the snap fastener 41 is generally U-shaped, and at least a portion of two opposite sides of the U-shaped snap fastener may be spaced apart. With such an arrangement, when being pressed by the user, the two sides of the U-shaped snap fastener can get close to each other to facilitate separation of the snap fastener 41 from the slot 42, so that the snap fastener 41 can be disengaged from the slot 42. Of course, the cross section of the snap fastener 41 may also have another shape, which is not limited herein.

Figure 17:
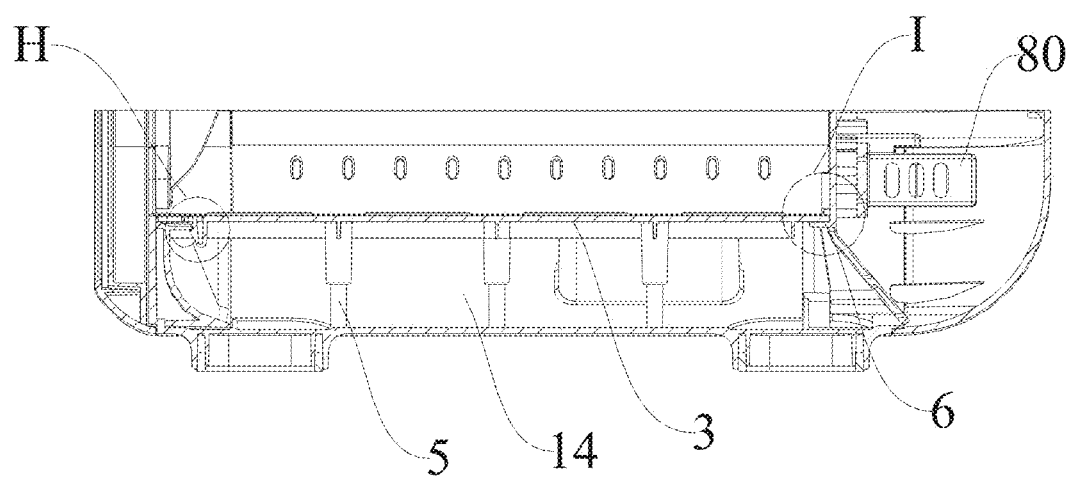
FIG. 17 is a partial cross-sectional view of the drying machine according to an embodiment of the present disclosure.

One end of the snap fastener 41 is connected to the inner wall of the groove 32, the other end of the snap fastener 41 has the snap portion 411, a limiting protrusion 412 is provided on a side of the snap fastener 41 facing the extension 15, and the limiting protrusion 412 and the snap portion 411 are respectively located on two sides of the extension 15 in a thickness direction (for example, in a vertical direction as shown in FIG. 17). Thus, during actual mounting, it is possible to snap-fit the extension 15 between the limiting protrusion 412 and the snap portion 411 to prevent the second partition plate 3 from movement, which in turn enhances the mounting stability of the second partition plate 3 and the box body 1.

Figure 15:
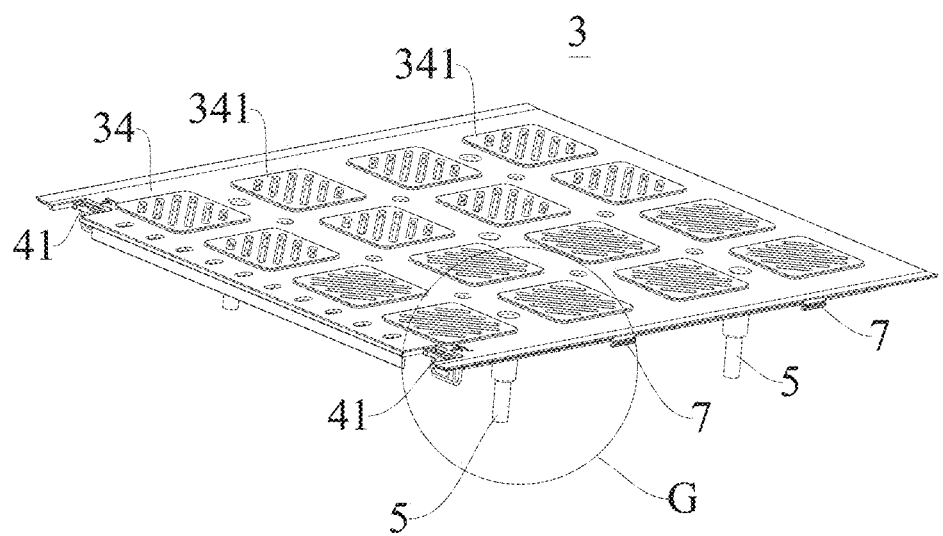
FIG. 15 is a schematic diagram of the second partition plate of the drying machine according to an embodiment of the present disclosure.

Further, as shown in FIG. 15, a side surface of the limiting protrusion 412 facing a side wall of the box body 1 obliquely extends toward the side wall of the box body 1 from bottom to top, and the thickness of the limiting protrusion 412 gradually increases from an end close to the bottom of the box body 1 to the end away from the bottom of the box body 1, so that a surface of the side of the limiting protrusion 412 facing the side wall of the box body 1 is formed as a bevel. Thus, on the one hand, a mutually abutting area between the extension 15 and the limiting protrusion 412 can be increased, and on the other hand, the space occupied by the limiting protrusion 412 can be decreased, so as to facilitate the disengagement of the snap fastener 41 together with the limiting protrusion 412 from the slot 42. Further, an end surface of the end of the limiting protrusion 412 away from the bottom of the box body 1 is adapted to the bottom of the extension 15, so as to ensure the mounting reliability of the extension 15 and the limiting protrusion 412. Optionally, the limiting protrusion 412 and the snap fastener 41 may be formed as one piece to improve the structural reliability.

Further, part of an upper surface of the extension 15 is formed as a first concave surface 151 recessed downwards. When the snap fastener 41 and the slot 42 are mounted or separated, the user can abut against the first concave surface 151 with his/her hand so as to improve the user's comfort during mounting or dismounting. For example, the first concave surface 151 may be an arc-shaped surface, so that the comfort can be further improved.

Figure 18:
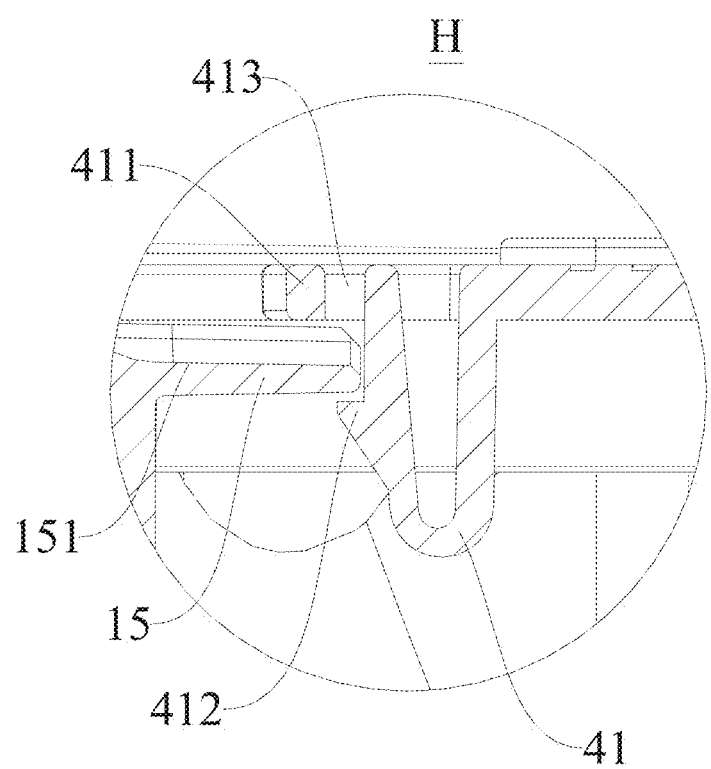
FIG. 18 is an enlarged view of part H circled in FIG. 17.

In some optional embodiments, as shown in FIG. 18, a through penetrating hole 413 is formed in the snap portion 411 to decrease the weight of the snap portion 411 and to achieve a lightweight design of the snap-fitting assembly 4, and it is conducive for the snap portion 411 to deform toward the penetrating hole 413 when the user presses the snap portion 411 to separate the snap portion 411 from the slot 42, so that the force of the user required for pressing the snap portion 411 can be decreased by virtue of the penetrating hole 413, facilitating quick mounting and dismounting of the second partition plate 3 by the user.

Figure 16:
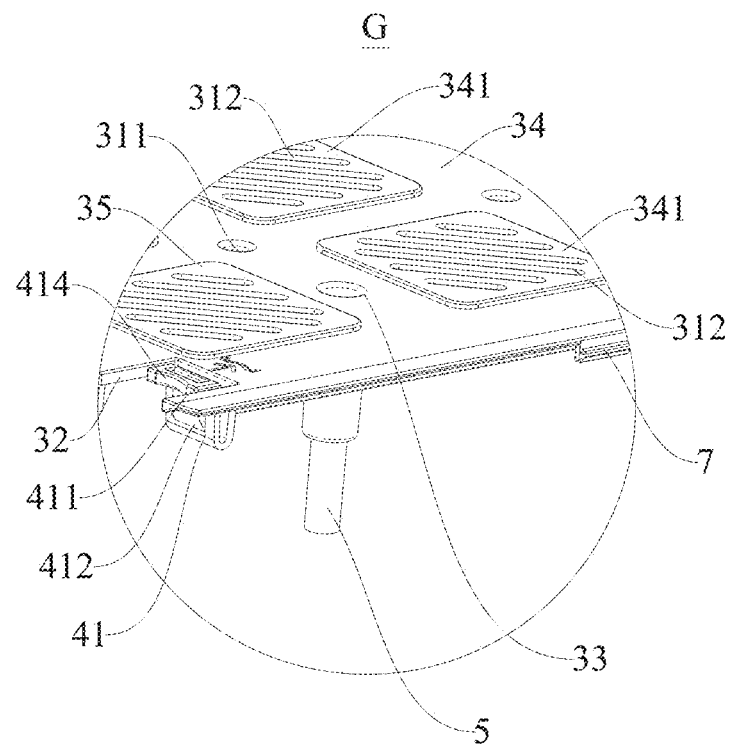
FIG. 16 is an enlarged view of part G circled in FIG. 15.

Referring to FIG. 16, at least part of the side surface of the snap portion 411 facing the side wall of the box body 1 is formed as a second concave surface 414 recessed in a direction away from the side wall of the box body 1, wherein the second concave surface 414 may be designed as another shape according to the requirement of the user, for example, the second concave surface 414 may be a circular arc surface, so that the hand of the user can fit the second concave surface 414 when the user holds it, increasing the contact area between the two, and thus the user can press the snap portion 411 with a small force, enhancing the practicability of the snap portion 411.

Optionally, the snap fastener 41 may be an elastic fastener, and the snap fastener 41 arranged in such a way that the snap fastener can elastically deform when the user applies a force to the snap fastener 41, so as to facilitate the separation of the snap fastener 41 from the slot 42 when the user presses the snap fastener 41, thereby implementing the dismounting or mounting of the two. In addition, the elastic member has a good recovery performance, and when the user stops applying the force to the snap fastener 41, the snap fastener 41 can recover to its shape before pressing by virtue of its own recovery ability, so as to facilitate the mounting and fit of the snap fastener 41 and the slot 42 and provide a good mounting reliability.

In some optional embodiments, the snap-fitting assembly 4 is located in the front of the box body 1. For example, when the user opens the box body 1, the mounting or dismounting of the second partition plate 3 and the box body 1 can be completed by mounting or dismounting the snap fastener 41 and the slot 42 such that the effect of improving the dismounting convenience can be provided, and the mounting and dismounting efficiency is improved.

Optionally, a plurality of snap-fitting assemblies 4 may be provided, and the plurality of snap-fitting assemblies 4 are spaced apart from each other. For example, two snap-fitting assemblies 4 may be provided, and the two snap-fitting assemblies 4 may be respectively provided on two sides of the box body 1 in a width direction (for example, the left-right direction as shown in FIG. 1), and during mounting or dismounting, the user may hold the two snap-fitting assemblies 4 respectively with his/her left and right hands, and accordingly can simultaneously mount or dismount the second partition plate 3 from the two sides of the second partition plate 3. The difficulty in mounting and dismounting the second partition plate 3 is reduced, and the detachable connection between the second partition plate 3 and the box body 1 can be firmly achieved.

Optionally, bulges for increasing a frictional force may be additionally provided on the second partition plate 3, and may allow the pet to be more stable on the second partition plate 3 for drying. The bulges may be elongated or square, which is not limited herein.

In some optional embodiments, the spacing between the second partition plate 3 and the bottom wall of the box body 1 is between 1-2 cm (including an endpoint value). It should be noted herein that the "spacing" refers to the distance between the bottom surface of the second partition plate 3 and the top of the bottom wall of the box body 1. The spacing between the second partition plate 3 and the bottom wall of the box body 1 may be 1 cm, or the spacing between the second partition plate 3 and the bottom wall of the box body 1 may also be 2 cm. With such an arrangement, the drying cavity 11 and the second accommodation cavity 14 can have a more reasonable height, an activity space for the pet can also be ensured, the ventilation in the box body 1 can be facilitated, and the fluidity of the airflow inside the box body 1 can be improved, and accordingly the drying efficiency can be improved.

According to some embodiments of the present disclosure, as shown in FIGS. 15-17, the bottom wall inside the box body 1 is provided with at least one supporting member 5, and the supporting member 5 can support the second partition plate 3. For example, a plurality of supporting members 5 may be provided, and the plurality of supporting members 5 may be respectively provided at an edge and the center of the second partition plate 3, wherein the supporting members 5 provided at the edge of the second partition plate 3 may be symmetrically arranged so as to ensure the supporting effect on the second partition plate 3 and the mounting stability of the second partition plate 3. Since a certain distance between the second partition plate 3 and the bottom wall of the box body 1 is provided, that is to say, the second partition plate 3 is considered to be suspended inside the box body 1, the second partition plate 3 has a certain weight itself and the pet will lie on the second partition plate 3, the second partition plate 3 and the pet on the second partition plate 3 can be well supported by the supporting members 5 so as to ensure a good drying effect.

For example, four supporting members 5 may be provided, the four supporting members 5 are distributed at a distance from each other; one end of each of the supporting members 5 is connected to the bottom wall of the box body 1, and the other end of the supporting member 5 can be supported on the second partition plate 3 to facilitate the connection between the second accommodation cavity 14 and the first accommodation cavity 12, so that the airflow can flow to the second accommodation cavity 14 through the first accommodation cavity 12 and enter the drying cavity 11 through the air outlet 31 for drying the pet; and the supporting members 5 dispersedly arranged do not interfere with the flow of the airflow and do not hinder the flow of the air. When the pet lies on the second partition plate 3, the air can dry the abdomen and other parts of the pet by means of the air outlet 31 in the second partition plate 3 to improve the drying efficiency. Optionally, the supporting member 5 may be a supporting frame or a supporting post.

Optionally, the second partition plate 3 may also be detachably connected to the supporting member 5 by means of the snap-fitting assembly 4. The snap fastener 41 of the snap-fitting assembly 4 is arranged on the second partition plate 3, and the slot 42 of the snap-fitting assembly 4 is formed in the supporting member 5. During mounting, the snap fastener 41 of the second partition plate 3 may be snap-fitted into the slot 42 in the supporting member 5 to implement the detachable connection between the second partition plate 3 and the box body 1.

Further, referring to FIG. 16, a mounting hole 33 may be formed in the second partition plate 3, and an end portion of the supporting member 5 is fitted in the mounting hole 33. Thus, on one hand, the mounting hole 33 can provide a positioning effect so as to facilitate the mounting of the supporting member 5 and the second partition plate 3, improving the mounting efficiency; on the other hand, the insertion fitting of the supporting member 5 in the mounting hole 33 may improve the supporting stability of the supporting member 5 to ensure the comfort of the pet during drying.

Optionally, a plurality of mounting holes 33 may be provided, the plurality of mounting holes 33 in one-to-one correspondence with the plurality of supporting members 5, and the plurality of mounting holes 33 are spaced apart from each other. For example, four mounting holes 33 may be provided, and the four mounting holes 33 in one-to-one correspondence with the four supporting members 5. Thus, when the second partition plate 3 is mounted, the mounting holes 33 can be directly aligned to upper ends of the supporting members 5 so that the upper ends of the supporting members 5 at least partially extend into the mounting holes 33 to prevent the separation of the second partition plate 3 from the supporting members 5, and the connecting stability of the second partition plate 3 and the supporting members 5 can be enhanced. Further, the second partition plate 3 is supported by the supporting members 5, so that the second partition plate 3 will not fall off when the pet is in the drying cavity 11, thereby enhancing the overall structural strength of the drying machine 100.

Figure 19:
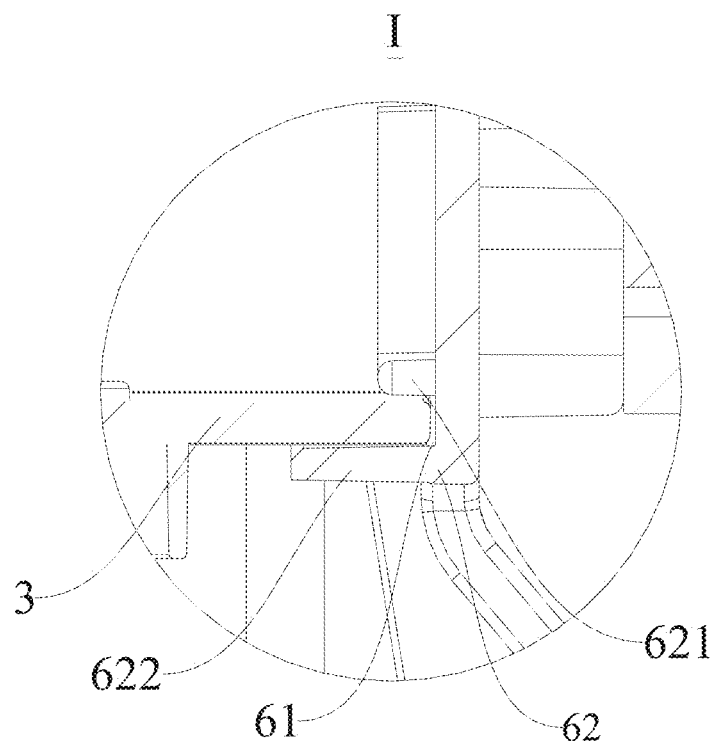
FIG. 19 is an enlarged view of part I circled in FIG. 17.

According to some embodiments of the present disclosure, as shown in FIG. 17, a mounting assembly 6 for mounting the second partition plate 3 is provided inside the box body 1, so that the second partition plate 3 can be prevented from being separated from the box body 1, which may in turn enhance the structural stability of the second partition plate 3. Further, as shown in FIG. 19, the mounting assembly 6 may comprise a sliding entrance 61 and a first mounting recess 62, and the second partition plate 3 may slide, in the box body 1, into the first mounting recess 62 along the sliding entrance 61. Thus, it is possible to reduce the difficulty in mounting and dismounting the second partition plate 3 and the box body 1, and to enhance the structural stability of the second partition plate 3. For example, the sliding entrance 61 may be a stop opening. The first mounting recess 62 may be an elongated groove. Two sliding entrances 61 may be provided, the two sliding entrances 61 may be symmetrically provided in two opposite inner sides of the box body 1, and the first mounting recess 62 is provided in the bottom of the box body 1 at a position corresponding to the sliding entrances 61. Where the first mounting recess 62 is provided in one side of the bottom of the box body 1, the slot 42 in the snap-fitting assembly 4 may be provided in the other side relative to the first mounting recess 62.

Specifically, when the second partition plate 3 is mounted on the box body 1, the second partition plate 3 can slide into the box body 1 along the sliding entrance 61 until the second partition plate reaches the first mounting recess 62, the second partition plate 3 is then snap-fitted to the box body 1 by means of the snap-fitting assembly 4, and the mounting assembly 6 further facilitates the entry of the second partition plate 3 into the box body 1, so that the efficiency of assembling the second partition plate 3 and the box body 1 can be improved.

Further, referring to FIG. 19, a first rib 621 and a second rib 622 are provided on the rear wall 13 in the box body 1, a rear end of the first rib 621 and a rear end of the second rib 622 are both connected to the rear wall 13 of the box body 1, and the second rib 622 is located below the first rib 621, such that the first mounting recess 62 is defined jointly by a lower side face of the first rib 621, an upper side face of the second rib 622, and the rear wall 13 of the box body 1, and the sliding entrance 61 is formed between a front end of the first rib 621 and a front end of the second rib 622.

Thus, during actual mounting, it is easy for the second partition plate 3 to slide into the box body 1 along the sliding entrance 61 until one end of the second partition plate 3 extends into the first mounting recess 62, and the second partition plate 3 can be limited by means of the first mounting recess 62, so that the second partition plate 3 is prevented from waggling or displacing, and the structural stability of the second partition plate 3 is enhanced.

Further, the width of the second rib 622 in a front-rear direction (e.g., the dimension in the front-rear direction as shown in FIG. 17) is greater than the width of the first rib 621 in the front-rear direction. Thus, when the second partition plate 3 is mounted in the first mounting recess 62, the contact area between the second rib 622 and the second partition plate 3 is increased to ensure the stability of supporting the second partition plate 3. Also, the second partition plate can be easy to mount and dismount, and the user can quickly mount and dismount the second partition plate 3, without influence of the first rib 621 on the mounting and dismounting of the second partition plate 3, which facilitates reducing difficulty in mounting and dismounting the second partition plate 3, improving the assembly efficiency of the drying machine 100.

In some optional embodiments, a limiting member for limiting the movement of the second partition plate 3 is provided in the box body 1. Thus, providing the limiting member allows to well fix the second partition plate 3 to prevent the second partition plate 3 from shifting, it can be ensured that the pet on the second partition plate 3 is effectively dried, the drying efficiency can be improved, and meanwhile, it can also be ensured that there is no play or movement between the second partition plate 3 and the box body 1 when the pet moves on the second partition plate 3.

Further, the limiting member may be a limiting hole, a first limiting block 7 which can be snap-fitted in the limiting hole is provided on the second partition plate 3, and the limiting hole and the first limiting block 7 can be snap-fitted or insertion-fitted to ensure the mounting stability of the second partition plate 3 and the box body 1. For example, the limiting hole may be a rectangular hole, and the first limiting block 7 may be a fastener that can be snapped into the small rectangular hole. In an embodiment of the present disclosure, four limiting holes may be provided, and the four limiting holes are respectively symmetrically provided in two opposite inner sides of the box body 1, four first limiting blocks 7 are also provided on the second partition plate 3, and the four first limiting blocks 7 are respectively symmetrically provided on the two opposite sides of the second partition plate 3. Thus, the first limiting blocks 7 on the second partition plate 3 are snap-fitted in the limiting holes in the box body 1 to allow to better fix the second partition plate 3 and prevent the second partition plate 3 from shifting, ensuring that the pet on the second partition plate 3 is effectively dried and improving the drying efficiency.

Figure 3:
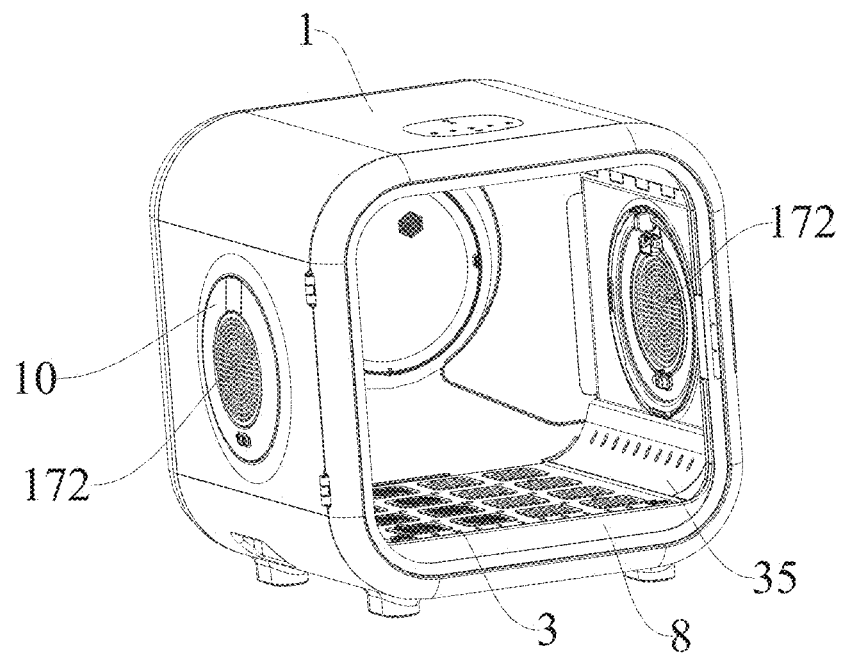
FIG. 3 is a schematic diagram of the drying machine according to an embodiment of the present disclosure, in which a fan wheel housing and a fan are not shown.
Figure 11:
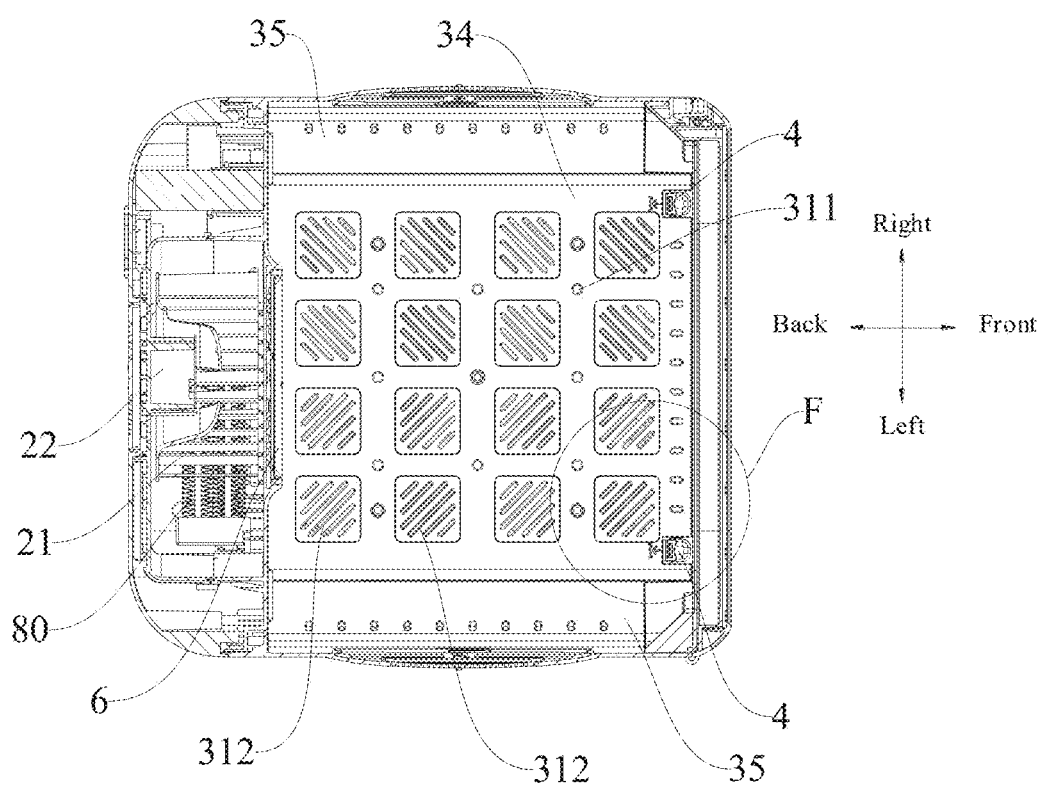
FIG. 11 is a cross-sectional view of the drying machine according to an embodiment of the present disclosure.
Figure 12:
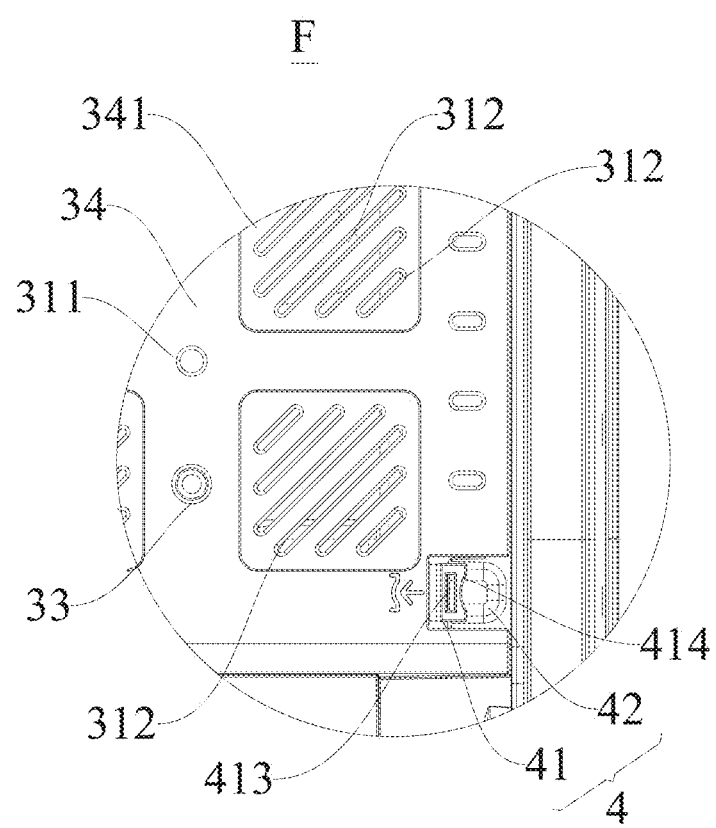
FIG. 12 is an enlarged view of part F circled in FIG. 11.

According to some embodiments of the present disclosure, the air outlet 31 comprises a plurality of air outlet orifices. The second partition plate 3 comprises a partition plate body 34 and two partition plate sections 35, wherein the two partition plate sections 35 are respectively arranged on the left side and the right side of the partition plate body 34, the two partition plate sections 35 extend obliquely upwards from bottom to top in a direction away from the center of the partition plate body 34, and a plurality of air outlet orifices are formed on both the two partition plate sections 35 and the partition plate body 34. Referring to FIGS. 1, 3 and 11, the second partition plate 3 may be a U-shaped partition plate, each of the partition plate sections 35 may be an arc-shaped partition plate protruding away from the partition plate body 34, a plurality of air outlet orifices may be distributed over the U-shaped partition plate, the pet may be placed on the partition plate body 34 of the U-shaped partition plate, and an airflow may be jetted from bottom to top through the plurality of air outlet orifices in the partition plate body 34, so as to facilitate drying the abdomen of the pet. The plurality of air outlet orifices of each of the partition plate sections 35 are arranged at a distance from each other in the length direction of the partition plate section 35, and the airflow is jetted obliquely upwards through the plurality of air outlet orifices in the two partition plate sections 35 to facilitate drying the back or other parts of the pet, thereby drying the fur of the pet all around, which may in turn improve the utilization rate of wind energy of the drying machine 100 and provide a high drying speed and a good drying effect. Providing the two partition plate sections 35 to extend obliquely upwards from the bottom to the top in the direction away from the center of the partition plate body 34 allows to direct the airflow in the second accommodation cavity 14 and to reduce a wind resistance to the airflow in the second accommodation cavity 14 so that the airflow can be rapidly blown into the drying cavity 11. It should be noted that the second partition plate 3 may be shaped to be as close as possible to the bottom wall of the box body 1 depending on the shape of the bottom wall of the box body 1, so as to provide better fit between the second partition plate 3 and the box body 1.

Optionally, the plurality of air outlet orifices in the partition plate body 34 may be square to increase the jetting area for the airflow, and the plurality of air outlet orifices in each partition plate section 35 can be circular to provide an air jetting assistance, and these air outlet orifices can work together to achieve a good drying effect.

In some optional embodiments, a plurality of a plurality of bosses 341 are provided on the partition plate body 34, the plurality of bosses 341 are arranged to be spaced apart from each other on the upper surface of the partition plate body 34, and the plurality of air outlet orifices in the partition plate body 34 include a plurality of first air outlet orifices 311 and a plurality of second air outlet orifices 312, the plurality of first air outlet orifices 311 are formed in the partition plate body 34, and the plurality of second air outlet orifices 312 are formed in the plurality of bosses 341. Thus, the airflow can be blown from the second accommodation cavity 14 to the drying cavity 11 through the plurality of first air outlet orifices 311 and the plurality of second air outlet orifices 312. In addition, providing the bosses 341 and forming the second air outlet orifices 312 in the bosses 341 enable upper ends of the first air outlet orifices 311 and upper ends of the second air outlet orifices 312 to be located at different levels, so that the first air outlet orifices 311 and the second air outlet orifices 312 can be different in air outflow height to prevent all the air outlet orifices from being completely blocking by the pet placed on the second partition plate 3, which makes the airflow incapable of sufficiently entering the drying cavity 11, so that the drying effect on the pet can be effectively ensured.

In some embodiments, a drain hole (not shown) is formed in the bottom wall of the box body 1. Providing the drain hole makes it possible to conveniently drain the water inside the box body 1 to the outside of the box body 1 so as to be conducive to ensure dry environment inside the box body 1.

The drying machine 100 may further comprise a stopper (not shown) that is detachably arranged at the above-mentioned drain hole to open or close the drain hole. When the stopper is mounted at the drain hole, the stopper can close the drain hole, and in this case, the water inside the box body 1 cannot be drained through the drain hole. For example, when the pet is placed inside the box body 1 for drying, the stopper may be mounted at the drain hole to close the drain hole so as to prevent the airflow from being dispersed through the drain hole to the outside of the box body 1, so that the drying efficiency and effect can be ensured.

When the stopper is removed from the drain hole, the drain hole is brought into an opened state, and the water inside the box body 1 can flow from the box body 1 through the drain hole. The stopper is detachably connected to the drain hole, so that the mounting or dismounting of the stopper can be facilitated, the user can select the closed or opened state of the drain hole according to actual requirements, and the use experience of the user can be improved.

Figure 4:
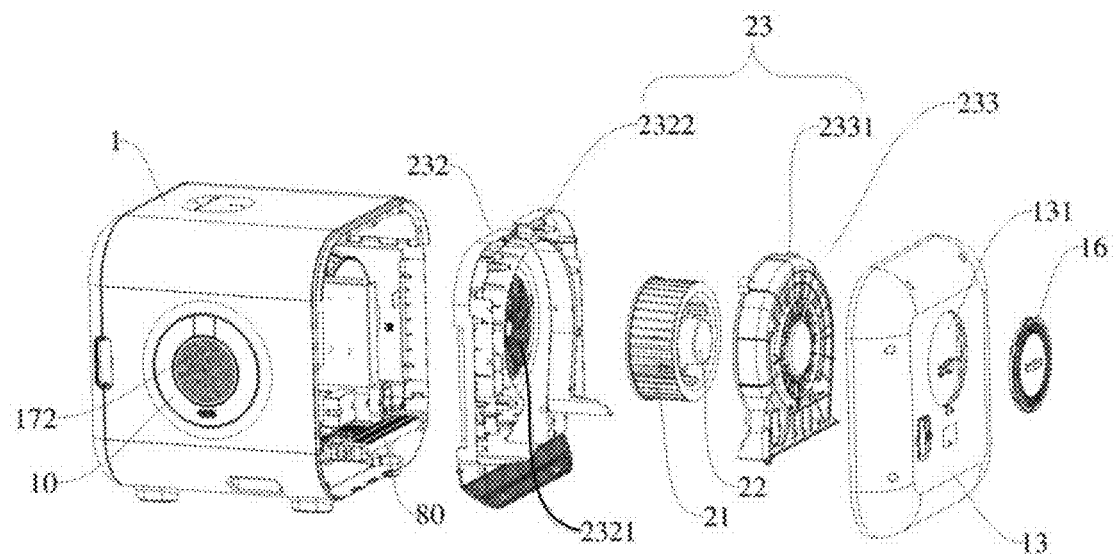
FIG. 4 is an exploded view of the drying machine according to an embodiment of the present disclosure.

According to some embodiments of the present disclosure, a heating assembly 80 is provided at the air channel outlet 2311 of the air channel 231. With reference to FIG. 4, the heating assembly 80 may extend in the length direction of the air outlet of the air channel 231, and the heating assembly 80 may increase the flow rate of the airflow and thus the utilization rate of wind energy, and may also rise the temperature of the airflow inside the second accommodation cavity 14 to achieve heating and drying functions, so that the pet in the drying machine 100 can feel comfortable and will not get sick due to only cold air blown by the drying machine 100, and the drying efficiency is also improved. In addition, when the drying machine 100 is used as a cat nest, the drying machine 100 may blow warm air in winter and cool air in summer by cooperatively using the fan wheel 21 and the heating assembly 80, so that the pet will be more comfortable in the drying machine 100. Optionally, the heating assembly 80 may be a Positive Temperature Coefficient (PTC) heater.

According to some embodiments of the present disclosure, a negative ion generator is provided on the first partition plate 232, and an output end of the negative ion generator extends into the first accommodation cavity 12. Thus, when the negative ion generator operates, negative ions generated by the negative ion generator can flow into the drying cavity 11 through the output end to sterilize and disinfect the airflow in the drying cavity 11.

An ozone disinfection apparatus is provided on the heating assembly 80. For example, the ozone disinfection apparatus may be an ozone disinfector or an ozone generator, and pet clothes or pet toys, etc. may be placed in the box body 1 for ozone disinfection, increasing the functionality of the drying machine 100 and further improving the practicability and utilization rate of the drying machine 100.

Further, the air channel 231 is a spiral air channel. Referring to FIG. 13, a projection of the spiral air channel on the first partition plate 232 is in the form of a spiral. Thus, providing the air channel 231 as the spiral air channel allows to increase the air outflow from the air channel outlet 2311.

Still further, a projection of at least a portion of the fan wheel housing 23 on the first partition plate 232 is in the form of a spiral. For example, in the example of FIG. 13, the projection of at least the portion of the fan wheel housing 23 on the first partition plate 232 is in the form of a Archimedean spiral. Thus, by virtue of the principle of the Archimedes spiral, the length of the air channel 231 can be shortened, the loss of wind energy is small, it can be ensured that the airflow blown from the air channel 231 can have a certain impact force, so that the drying function of the drying machine 100 can be well realized.

According to some embodiments of the present disclosure, referring to FIG. 13, the air channel 231 has the air channel outlet 2311, and the cross-sectional area of at least a portion of the air channel 231 gradually increases toward the air channel outlet 2311 in a circumferential direction of the fan wheel 21. Thus, the airflow can be forced from a narrow portion to a wide portion in an extension direction of the air channel 231 and finally blown out at the air channel outlet 2311 with a reduced pressure intensity, so that it is possible to ensure the airflow blown out from the air channel outlet 2311 having a certain impact force, and the drying efficiency of the drying machine 100 can thus be improved.

According to some embodiments of the present disclosure, as shown in FIG. 4, the fan wheel housing 23 is arranged on at least one of the first partition plate 232 and the rear wall 13. The fan wheel housing 23 may be arranged on one of the first partition plate 232 and the rear wall 13; and optionally, the fan wheel housing 23 may also be provided on both of the first partition plate 232 and the rear wall 13. Thus, the drying machine 100 may be made compact in terms of structure.

Further, the drying machine 100 further comprises an electric motor support 233. The fan wheel housing 23 comprises a first fan wheel housing 2322 and a second fan wheel housing 2331, wherein the first fan wheel housing 2322 is arranged on the first partition plate 232, the second fan wheel housing 2331 is arranged on the electric motor support 233, and the second fan wheel housing 2331 and the first fan wheel housing 2322 jointly define a fan wheel accommodation cavity for accommodating the fan wheel 21. Referring to FIG. 4, the electric motor support 233 is arranged between the fan wheel 21 and the rear wall 13, an electric motor 22 is provided inside the fan wheel accommodation cavity, an output shaft of the electric motor 22 is fixed to the fan wheel 21, the electric motor 22 is mounted on the second fan wheel housing 2331, and the second fan wheel housing 2331 can support the electric motor 22, so that the electric motor 22 is stable and reliable during operation, and the drying effect can thus be improved. The electric motor support 233 may be an annular electric motor support adapted to the first fan wheel housing 2322, the electric motor 22 may be positioned at an inner ring of the annular electric motor support, and a ventilation hole parallel to the rotation axis of the fan wheel 21 is formed in the annular electric motor support, so that the airflow outside the drying machine 100 may flow toward the fan wheel 21 through the second air inlet 131 and the ventilation hole.

Still further, the electric motor support 233 is formed with an air inlet hole that runs therethrough in an axial direction of the fan wheel 21, the electric motor support 233 is in sealed connection with the rear wall 13 on a peripheral side of the air inlet hole, and outside air sucked by the fan wheel 21 sequentially passes through the second air inlet 13 and the air inlet holes and enters the fan wheel accommodation cavity. Thus, the outside air can directly enter the fan wheel accommodation cavity through the second air inlet 13 and the air inlet holes of the electric motor support 233, and the drying efficiency can be improved.

In some optional embodiments, the electric motor support 233 is detachably connected to the first partition plate 232. Thus, the mounting and dismounting of the electric motor support 233 are facilitated.

In some optional embodiments, referring to FIG. 4, the rear surface of the first partition plate 232 extends backwards from the first fan wheel housing 233. With such an arrangement, the first fan wheel housing 233 and the first partition plate 232 can be integrally formed, so that the steps of assembling the drying machine 100 can be decreased, and the assembly efficiency of the drying machine 100 can thus be improved.

Optionally, the fan wheel 21 may be a forward-inclined fan wheel that can use a centrifugal force to apply work and that can increase the pressure of the airflow to compress the airflow in the air channel 231, such that the airflow jetted through the air channel outlet 2311 has a certain impact force so as to better achieve the drying function.

According to some embodiments of the present disclosure, the fan wheel 21 is provided as an axially through fan wheel. For example, a hub of the fan wheel 21 may be formed with a plurality of ventilation holes therethrough, and the plurality of ventilation holes may be arranged at a distance from each other in a circumferential direction of the fan wheel 21. When the fan wheel 21 operates, the airflows inside and outside the box body 1 can enter the fan wheel 21 in the axial direction of the fan wheel 21, and are then radially expelled by blades of the fan wheel 21, such that the airflow accumulates and is compressed in the air channel 231 and flows toward the drying cavity 11 of the box body 1 through the air channel outlet 2311. The ventilation holes can allow the outside airflow to directly enter the fan wheel 21 and increase the airflow entering the fan wheel 21, such that the air inside and outside the drying machine 100 can circulate fully, and comfortable drying environment can thus be provided.

In some optional embodiments, a fur filter screen is provided at the first air inlet 2321, and a dust filter screen 16 is provided at the second air inlet 13. As shown in FIG. 4, the dust filter screen 16 is arranged on a side of the fan wheel 21 away from the inside of the box body 1, and the fur filter screen is arranged on a side of the fan wheel 21 close to the inside of the box body 1. The dust filter screen 16 may be arranged directly at the second air inlet 13 of the rear wall 13 of the box body 1. When the pet is dried in the drying machine 100, the fur of the pet tends to shed, and the fur filter screen can filter out the fur in the airflow entering the fan wheel 21 in the box body 1, ensuring that the fan wheel 21 can operate normally. In addition, since the environment where the drying machine 100 is located may be a crowded place such as a shop and the outdoor, the airflow outside the box body 1 inevitably contains dust, and the dust filter screen 16 can filter out the dust in the airflow outside the box body 1 entering the fan wheel 21 to enable the fan wheel 21 to smoothly achieve the functions of inside and outside air suction and can filter out the impurities in the airflow, such the effective service life of the drying machine 100 can be prolonged, and a drying machine 100 with fresh inside air and comfortable environment can also be provided.

Optionally, in the drying machine 100, a transition area between the position of the air channel outlet 2311 of the air channel 231 and the bottom wall of the box body 1 is shaped as a circular arc chamfer and may specifically be shaped as a quadrant. With such an arrangement, transitional air guiding can be effectively smoothed, and noise can be effectively reduced.

According to some embodiments of the present disclosure, at least one cat stroking opening 171 is formed in the box body 1, and a cat stroking door 172 is provided at the cat stroking opening 171 to open or close the cat stroking opening 171. With reference to FIGS. 1 and 3, when the pet is positioned inside the box body 1 for drying, the user can push the cat stroking door 172 toward the inside of the box body 1 or pull open it toward the outside of the box body 1, so as to open the cat stroking opening 171, and stretch one hand into the cat stroking opening 171 to stroke the pet inside the box body 1 and calm the pet down, facilitating smooth drying, improving the drying effect, and improving the comfort of the pet during drying. Also, the user can stretch one hand into the cat stroking opening 171 to touch the fur of the pet, so as to determine the degree of drying and to determine whether the drying is completed or additional duration for drying is needed, thereby improving the drying efficiency; and the cat stroking door 172 covers the cat stroking opening 171 to prevent the feet of the pet from stretching out from the cat stroking opening 171, ensuring that the whole body of the pet is dried. The cat stroking opening 171 has a small open area and may be designed only for a person to stretch or retract his/her hands, so that the pet can be prevented from escaping from the box body 1.

For example, as shown in FIG. 1, the user can push the cat stroking door 172 from the outside of the box body 1 to the inside of the box body 1 to open the cat stroking opening 171. On one hand, with such an arrangement, it is convenient and labor-saving for the user; and on the other hand, the pet can be prevented from opening the cat stroking door 172 in the box body 1 to ensure the drying efficiency.

Figure 23:
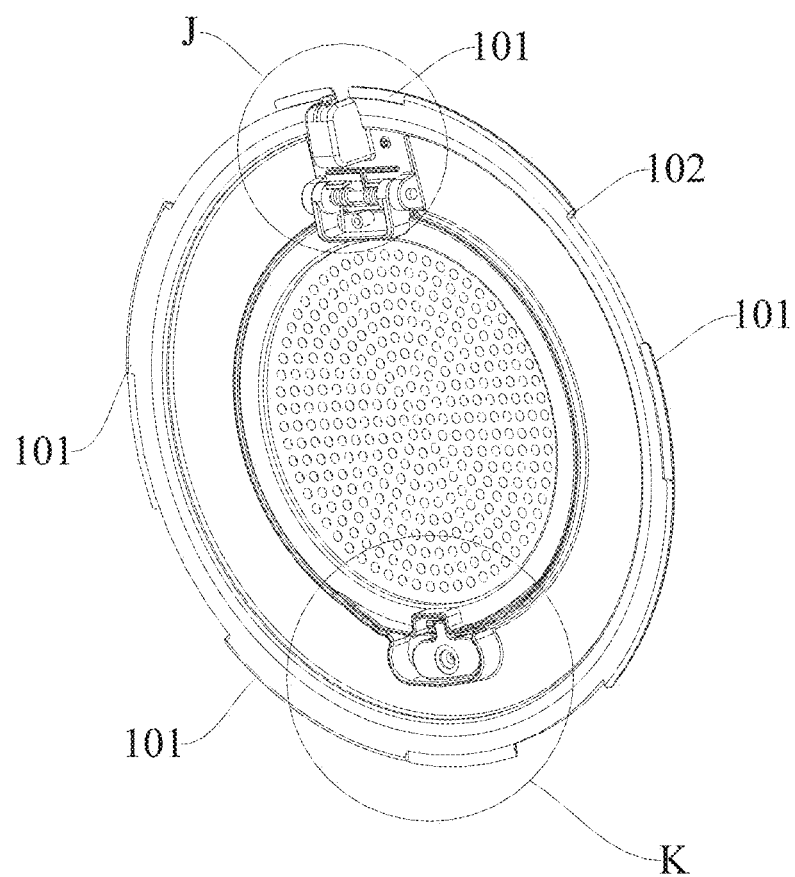
FIG. 23 is a schematic diagram showing the cat stroking door and the viewing window of the drying machine at still another view angle according to an embodiment of the present disclosure.
Figure 24:
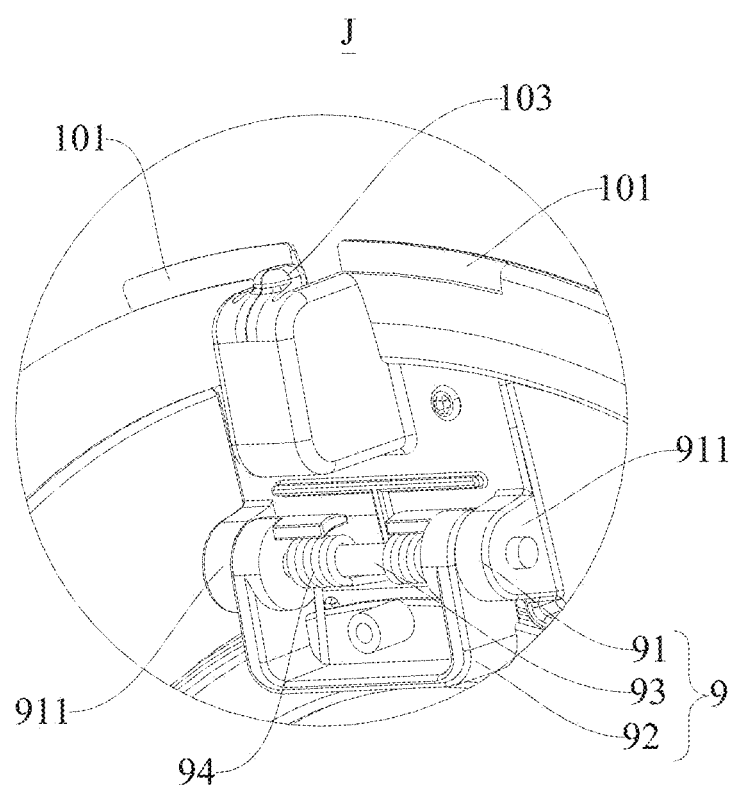
FIG. 24 is an enlarged view of part J circled in FIG. 23.

Further, referring to FIGS. 23 and 24, the cat stroking door 172 is pivotably connected to the box body 1 by means of a pivoting assembly 9 to facilitate the opening and closing of the cat stroking door 172. The door is labor-saving and easy to open or close, the connecting stability of the box body 1 and the cat stroking door 172 can also be improved, and the reliability during pivoting of the cat stroking door 172 can be ensured. The pivoting assembly 9 comprises a first mounting portion 91, a second mounting portion 92 and a pivot shaft 93, wherein the first mounting portion 91 is arranged on the box body 1, the second mounting portion 92 is arranged on the cat stroking door 172, and the pivot shaft 93 penetrates the first mounting portion 91 and the second mounting portion 92 to allow the cat stroking door 172 to be pivotable relative to the box body 1. Thus, providing the first mounting portion 91 and the second mounting portion 92 allows for ease of the mounting of the pivot shaft 93, and the stability during pivoting can be improved.

Still further, as shown in FIG. 23, the drying machine 100 further comprises at least one torsion spring 94, wherein the torsion spring 94 is sleeved on the pivot shaft 93, and the torsion spring 94 normally forces the cat stroking door 172 in a closing direction of the cat stroking opening 171. For example, the torsion spring 94 may have an abutting portion, one end of the abutting portion may abut against the side wall of the box body 1, and the other end of the torsion spring 94 may abut against the second mounting portion 92. The pivot shaft 93 may penetrate the torsion spring 94 in the length direction of the torsion spring 94, and two ends of the pivot shaft are respectively connected to two ends of a mounting seat.

It can be understood that the torsion spring 94 is a mechanical force accumulation structure and has a self-resetting function; the torsion spring 94 has a certain force to fasten the cat stroking door 172 thereon, and a certain force is required for opening the cat stroking door 172, making it difficult for the pet to open the door by itself, so as to ensure that the whole body of the pet is dried inside the box body 1 and to improve the drying effect. When a person's hands exit the cat stroking opening 171, the cat stroking door 172 can automatically return by means of the torsion spring 94 to continue to cover the cat stroking opening 171 and to prevent the pet from escaping or other impurities from entering the box body 1, which may affect the drying effect.

According to some embodiments of the present disclosure, one side of the box body 1 is open, and a door body 8 is arranged on the above-mentioned side of the box body 1 to open or close the above-mentioned side of the box body 1. For example, a front side of the box body 1 is open, and the door body 8 may be arranged on the front side of the box body 1 to open or close the front side of the box body 1, so that the user can easily place the pet into the box body 1 or take the pet out of the box body 1. Alternatively, an upper side of the box body 1 is opened, the door body 8 may be arranged on the upper side of the box body 1 to open or close the upper side of the box body 1 so as to reduce the possibility of escaping of the pet, and a specific position of the door body 8 mounted on the box body 1 can be specifically arranged according to actual requirements, which is not limited herein.

In some optional embodiments, as shown in FIG. 23, the first mounting portion 91 may comprise two mounting lugs 911 spaced apart from each other, the second mounting portion 92 is located between the two mounting lugs 911, and the pivot shaft 93 penetrates the two mounting lugs 911 and the second mounting portion 92, so that the mounting reliability of the pivot shaft 93 and the first mounting portion 91 and of the pivot shaft 93 and the second mounting portion 92 can be ensured, and smooth pivoting of the cat stroking door 172 can be facilitated.

The two mounting portions can limit the position of the torsion spring 94 to prevent the torsion spring 94 from being disengaged from the pivoting assembly 9, and the pivot shaft 93 can prevent the torsion spring 94 from deformation, such that the connection between the cat stroking door 172 and the box body 1 is more secure and effective for a long time, and the effective service life of the drying machine 100 is ensured.

According to some specific embodiments of the present disclosure, as shown in FIGS. 1 and 3, an opening 17 is formed in the box body 1, a removable viewing window 10 is provided at the opening 17, and the cat stroking opening 171 is formed in the viewing window 10. Providing the viewing window 10 makes it convenient for the user to observe the internal environment inside the box body 1, and the user can observe the conditions of the pet without opening the cat stroking door 172 in order to timely watch the mood of the pet, so that a smooth drying process can be provided, the pet can be pleasant, and the practicability of the drying machine 100 can thus be improved. For example, the viewing window 10 may be made of a transparent material to further facilitate viewing of the pet inside the box body 1. The viewing window 10 may be adapted to the cat stroking door 172 in terms of shape, for example, the viewing window 10 may be ring-shaped.

Figure 20:
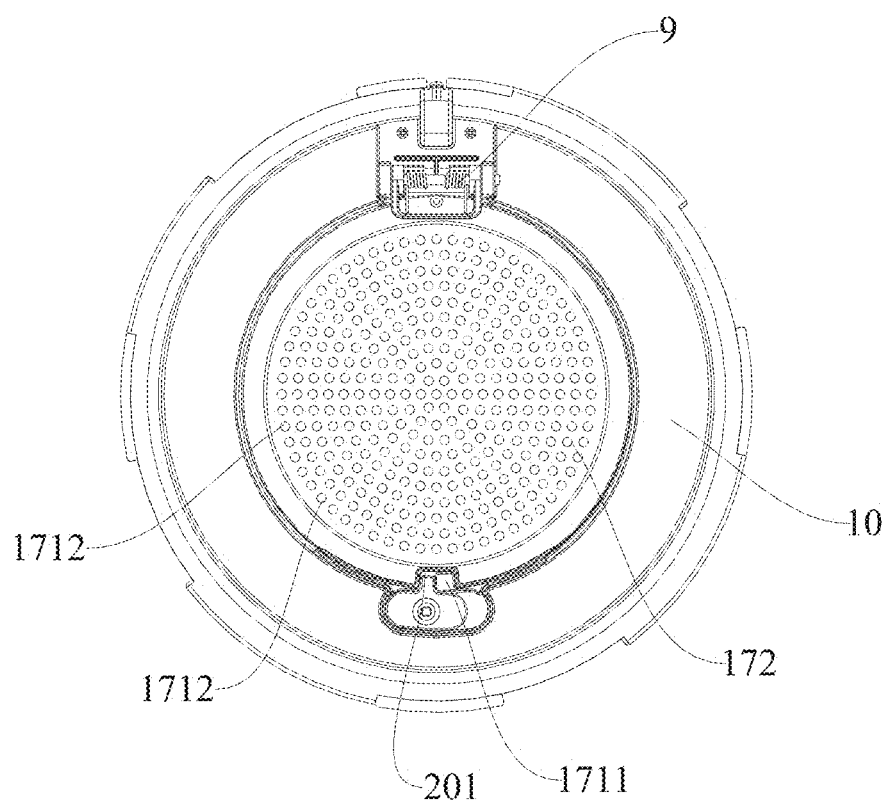
FIG. 20 is a schematic diagram of a cat stroking door and a viewing window of the drying machine according to an embodiment of the present disclosure.

Further, referring to FIG. 20, one end (e.g., an upper end as shown in FIG. 1) of the cat stroking door 172 is pivotably connected to the viewing window 10 by means of the pivoting assembly 9, and a locking assembly 20 is provided between the other end (e.g., a lower end as shown in FIG. 1) of the cat stroking door 172 and the viewing window 10. The cat stroking door 172 is suitable for opening the cat opening 171 when the locking assembly 20 is unlocked, and the cat stroking door 172 is fixed to the viewing window 10 when the other end of the cat stroking door 172 is locked by the locking assembly 20. Thus, providing the locking assembly 20 allows the cat stroking door 172 to be locked to the viewing window 10, and the locking assembly 20 needs to be unlocked first when a person wishes to open the cat stroking door 172, which can prevent the cat stroking door 172 from being opened by accident. The locking assembly 20 may be a locking fastener.

Figure 25:
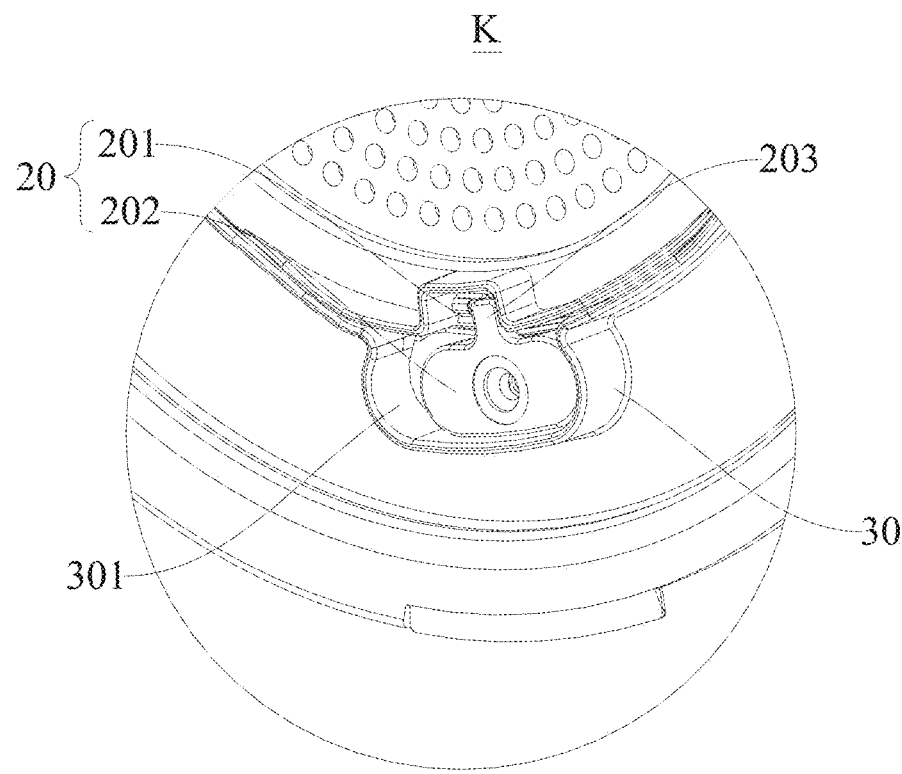
FIG. 25 is an enlarged view of part K circled in FIG. 23.
Figure 26:
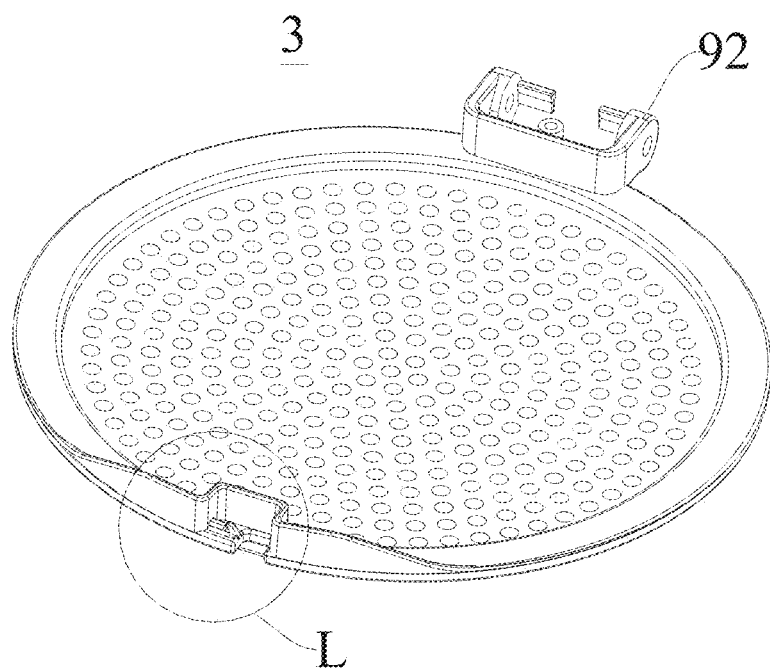
FIG. 26 is a schematic diagram showing the cat stroking door and a second mounting portion of the drying machine according to an embodiment of the present disclosure.

Further, with reference to FIG. 25, the locking assembly 20 comprises a locking slot 201 and a locking member 202, wherein the locking slot 201 is formed in the cat stroking door 172, the locking member 202 is movably arranged on the viewing window 10, a locking protrusion 203 is provided on the locking member 202, and the fitting between the locking protrusion 203 and the locking slot 201 can facilitate the adjustment of locked and unlocked states of the locking assembly 20 and can increase the contact area and improve the mounting reliability. When the locking protrusion 203 is fitted in the locking slot 201, the cat stroking door 172 is fixed to the viewing window 10, and when the locking protrusion 203 is separated from the locking slot 201, the cat stroking door 172 is suitable for opening the cat stroking opening 171 so as to adjust the locked and unlocked states of the locking assembly 20, and a high stability of fixing of the two in the locked state is provided. For example, at least one of the locking member 202 and the locking slot 201 is made of a deformable material in order that the locking protrusion 203 can move into the locking slot 201 to provide the locked state. As shown in FIG. 25, the locking protrusion 203 is provided with a projection 2031, and the projection 2031 may protrude from the locking protrusion 203 in the thickness direction of the locking protrusion 203 to facilitate the fitting between the locking protrusion 203 and the locking slot 201.

Figure 27:
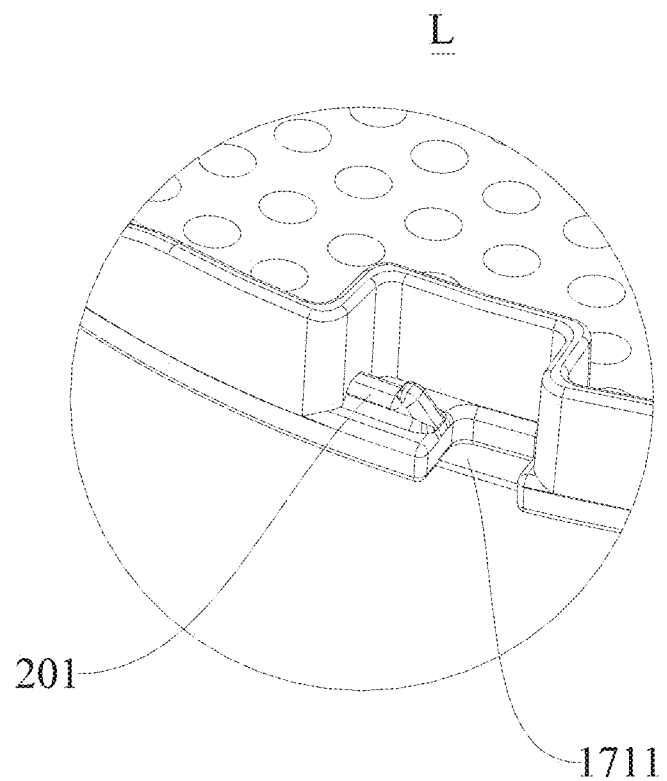
FIG. 27 is an enlarged view of part L circled in FIG. 26.
Figure 28:
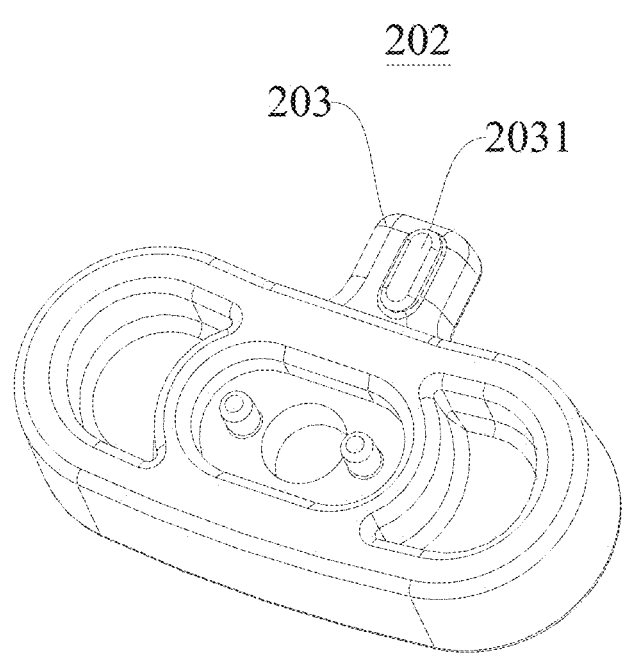
FIG. 28 is a schematic diagram of a locking member of the drying machine according to an embodiment of the present disclosure.

In some optional embodiments, as shown in FIG. 27, the cat stroking door 172 is formed with an avoidance opening 1711, the avoidance opening 1711 is arranged adjacent to the locking slot 201. When the locking protrusion 203 is separated from the locking slot 201, the locking protrusion 203 is opposite to the avoidance opening 1711. Thus, when the locking assembly 20 is in the unlocked state, the locking protrusion 203 can pass through the avoidance opening 1711, such that the cat stroking door 172 can be pivoted inwards or outwards to open the cat stroking opening 171, resulting in a structural reliability.

Further, as shown in FIG. 27, the locking slot 201 and the avoidance opening 1711 may be arranged in a circumferential direction of the cat stroking door 172, and the locking member 202 is movable in the circumferential direction of the cat stroking door 172. Thus, the locking member 202 may be moved in the circumferential direction of the cat stroking door 172. For example, the locking member 202 slidably fits with the viewing window 10 to improve the smoothness of movement, improving the use experience of the user.

In some optional embodiments, referring to FIG. 25, a barrier plate 30 extending toward the center of the box body 1 is provided on the viewing window 10, a second mounting recess 301 is defined between the barrier plate 30 and the viewing window 10, and the locking member 202 is movably arranged in the second mounting recess 301. Providing the barrier plate 30 makes it possible to prevent the pet from touching the locking member 202 by accident, which may change the locked or unlocked state of the locking member 202, so that the use safety of the drying machine 100 can be improved. According to some embodiments of the present disclosure, as shown in FIG. 23, a side at an edge of the opening 17 in a thickness direction is provided with a plurality of snap-fitting sections 173 arranged at a distance from each other in the circumferential direction of the cat stroking door 172, each snap-fitting section 173 is spaced apart from the edge of the opening 17 to define a snap-fitting groove 174, and a mounting opening 175 is defined between two adjacent snap-fitting sections 173. An peripheral edge of the viewing window 10 is provided with a plurality of flange sections 101 arranged at a distance from each other in the circumferential direction of the cat stroking door 172, and each of the plurality of flange sections 101 passes through a corresponding mounting opening 175 and is rotated relative to the opening 17 to be fitted in a corresponding snap-fitting groove 174. Thus, it is possible to detachably connect the box body 1 to the viewing window 10, the design is ingenious, and the efficiency of mounting and dismounting is high, such that the dismounting or mounting of the viewing window 10 can be implemented by rotating the viewing window 10, and positioning is facilitated. For example, some of the plurality of flange sections 101 may pass through corresponding mounting openings 175 and may be rotated relative to the openings 17 to be fitted in corresponding snap-fitting grooves 174.

Figure 22:
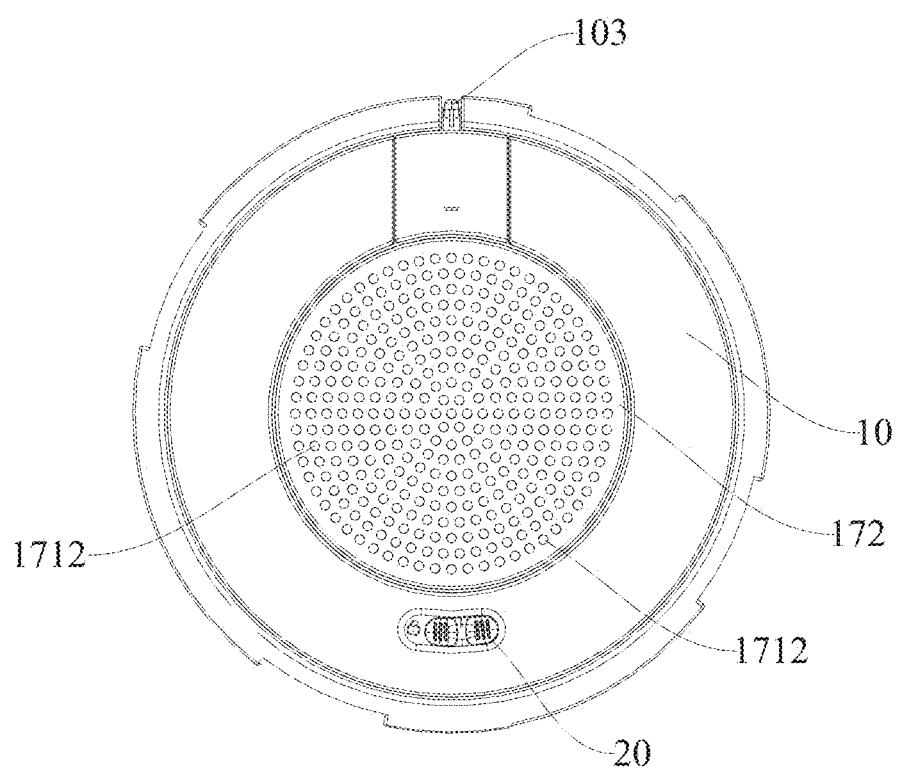
FIG. 22 is a schematic diagram showing the cat stroking door and the viewing window of the drying machine at another view angle according to an embodiment of the present disclosure.

Further, as shown in FIGS. 22 and 23, a first stopping protrusion 1731 is provided at one end of at least one snap-fitting section 173 in the circumferential direction, a second stopping protrusion 102 is provided at one end of at least one flange section 101 in the circumferential direction, the second stopping protrusion 102 cooperates with the first stopping protrusion 1731 to limit continuous rotation of the cat stroking door 172 relative to the opening 17. During dismounting, when a plurality of flange sections 101 are respectively fitted in a plurality of corresponding snap-fitting grooves 174, the first stopping protrusion 1731 can abut against the second stopping protrusion 102 to prevent further rotation of the cat stroking door 172 relative to the box body 1. Providing the two stopping protrusions allows for an improved accuracy of mounting, and allows to facilitate positioning. For example, one end of the flange section 101 may be fitted in a corresponding snap-fitting groove 174, and the other end of the flange section 101 may be provided with a second stopping protrusion 102.

Figure 2:
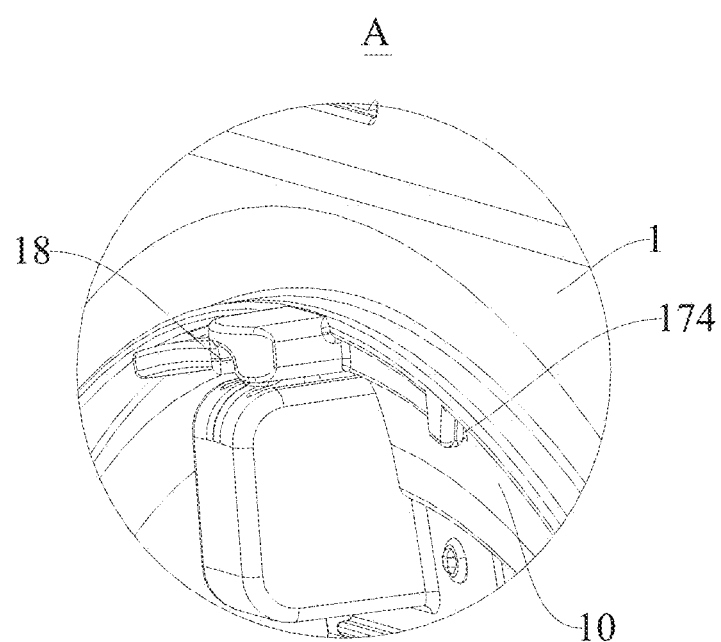
FIG. 2 is an enlarged view of part A circled in FIG. 1.
Figure 9:
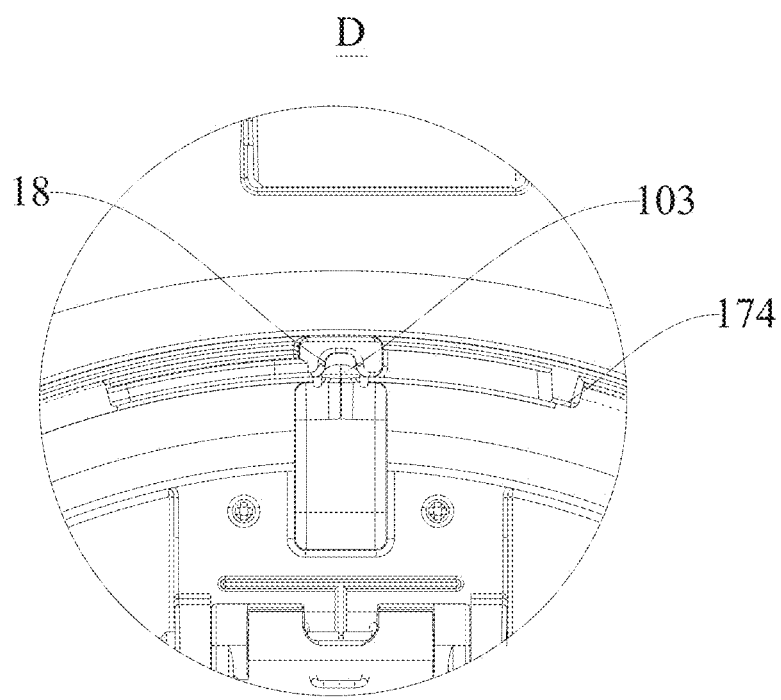
FIG. 9 is an enlarged view of part D circled in FIG. 7.
Figure 10:
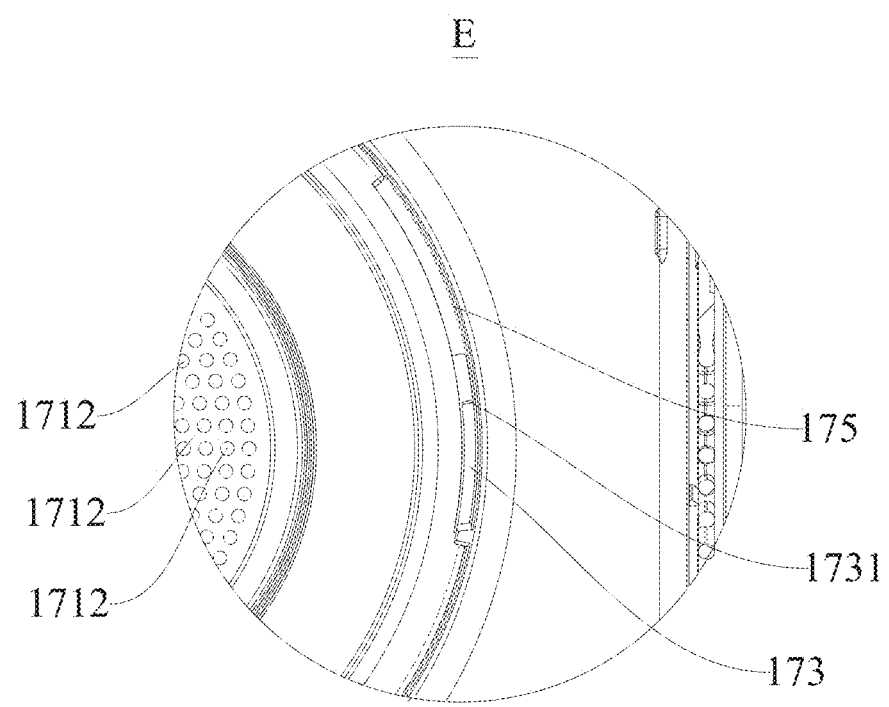
FIG. 10 is an enlarged view of part E circled in FIG. 7.
Figure 21:
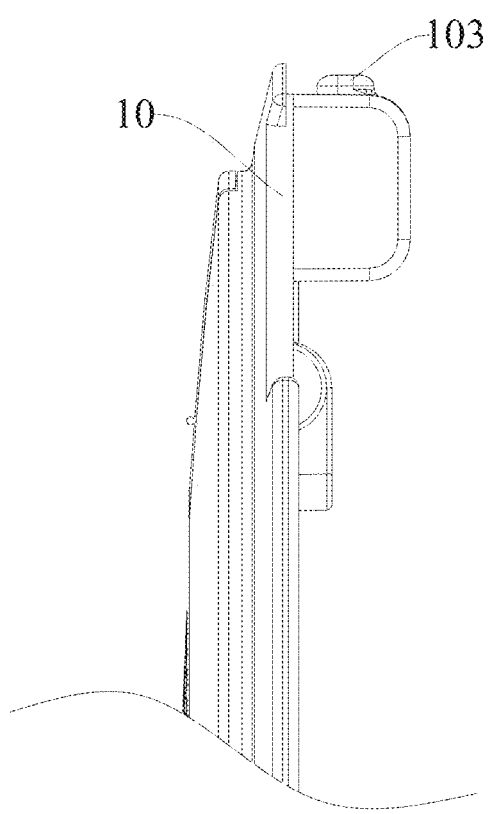
FIG. 21 is a side view of a partial structure of the viewing window according to an embodiment of the present disclosure.

In some examples, referring to FIGS. 2 and 21 in combination with FIGS. 9 and 23, a limiting groove 18 is formed in the box body 1, a second limiting block 103 is provided on the viewing window 10, and when the flange sections 101 are fitted in the snap-fitting grooves 174, the second limiting block 103 is fitted in the limiting groove 18 to limit the rotation of the cat stroking door 172 relative to the opening 17. The second limiting block 103 provided on the viewing window 10 can be snap-fitted to the limiting groove 18 and inserted into the limiting groove 18 when rotated together with the viewing window 10. By means of the fitting between the second limiting block 103 and the limiting groove 18, the positioning is facilitated, the fixing of the viewing window 10 can be stable on the box body 1, and the viewing window is not easily damaged by the pet in the box body 1. For example, the limiting groove 18 and the second limiting block 103 may be located at the upper end of the drying machine 100 to further reduce the possibility of damages to the two caused by the pet. For example, an opening of the limiting groove 18 may face the second limiting block 103. When the user applies a large acting force, the second limiting block 103 may be forced into the limiting groove 18 in the circumferential direction of the viewing window 10, achieving the limiting fixation of the second limiting block 103 and the limiting groove 18.

For example, during mounting, the description is given by taking the direction from the inner side face of the box body 1 to the outer side face of the box body 1 as an example, at the beginning of mounting the viewing window 10, the plurality of flange sections 101 are located at the corresponding mounting openings 175 in this case, the plurality of flange sections 101 can be fitted in the corresponding snap-fitting grooves 174 by rotating the viewing window 10 counterclockwise, the first limiting block 7 can deform to extend into the limiting groove 18 and then return to its original state, and will not continue moving under the limiting of a side wall of the limiting groove 18, so as to realize the relative fixing of the two. During dismounting, a clockwise acting force is applied to rotate the viewing window 10 such that the second limiting block 103 exits the limiting groove 18, and the viewing window 10 can be rotated in the circumferential direction of the opening 17 in this case. When the flange sections 101 completely exit the snap-fitting grooves 174, the flange sections 101 are located at the corresponding mounting openings 175, and the viewing window 10 can be dismounted from the box body 1 so as to remove the viewing window 10. When the first stopping protrusion 1731 abuts against the second stopping protrusion 102, the viewing window 10 cannot continue rotating.

According to some embodiments of the present disclosure, the wall forming the drying cavity 11 is formed with at least one through ventilation hole 1712. For example, as shown in FIGS. 4, 20, 22 and 23, a plurality of through ventilation holes 1712 may be formed in the cat stroking door 172, and the ventilation holes 1712 can facilitate ventilation of the inside of the box body 1 of the drying machine 100, so that the pet in the box body 1 can breathe fresh air and feel comfortable. Of course, the ventilation holes 1712 may also be formed in the door body 8. In addition, a nameplate may be provided on the viewing window 10, texts, patterns, or other contents may be imprinted on the nameplate to facilitate a diversified design of the drying machine 100.

In some optional embodiments, in combination with FIGS. 1 and 3, two cat stroking openings 171 are provided, and the two cat stroking openings 171 are respectively formed in a left side wall and a right side wall of the box body 1. Two cat stroking doors 172 are provided, and the two cat stroking doors 172 are respectively provided at the two cat stroking openings 171 to respectively open or close the corresponding cat stroking openings 171. Thus, the user can further conveniently observe the pet, and the user can observe or stroke the pet from a plurality of perspectives to improve the experience.

According to some embodiments of the present disclosure, as shown in FIGS. 5-8, a placement slot 19 is formed in the box body 1, and a fragrance box 40 is removably arranged in the placement slot 19 by means of a magnetic attraction assembly, such that the connection between the fragrance box 40 and the placement slot 19 is relatively simple, facilitating the mounting and dismounting of the fragrance box 40. The fragrance box 40 has a first configuration and a second configuration in the placement slot 19, and at least one through hole 4015 is formed in the fragrance box body 19. When the fragrance box 40 is in the first configuration, the interior of the fragrance box 410 is not in communication with the interior of the box body 1, and when the fragrance box 40 is in the second configuration, the interior of the fragrance box 40 is in communication with the interior of the box body 1 through the through holes 4015.

Figure 5:
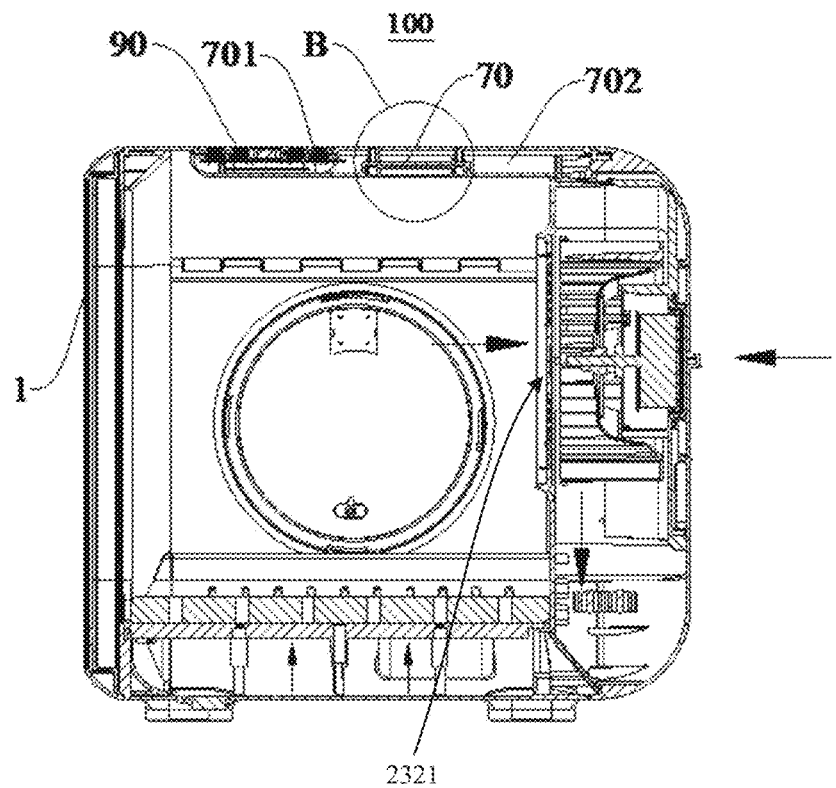
FIG. 5 is a schematic diagram of a fragrance box of the drying machine in a first configuration according to an embodiment of the present disclosure.
Figure 6:
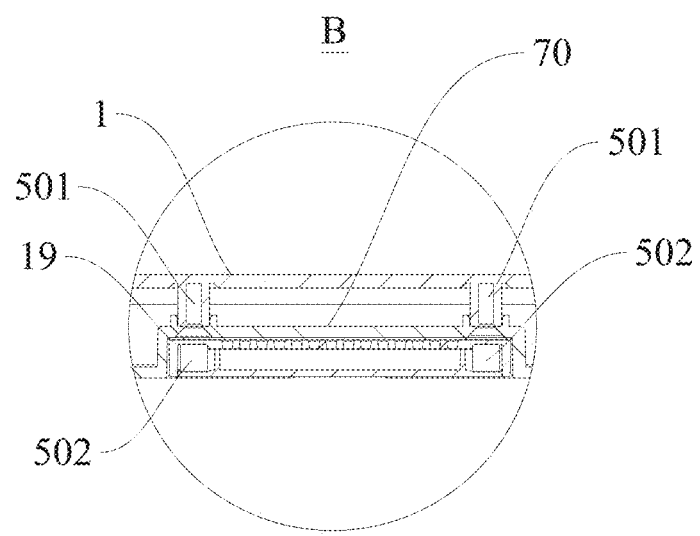
FIG. 6 is an enlarged view of part B circled in FIG. 5.
Figure 7:
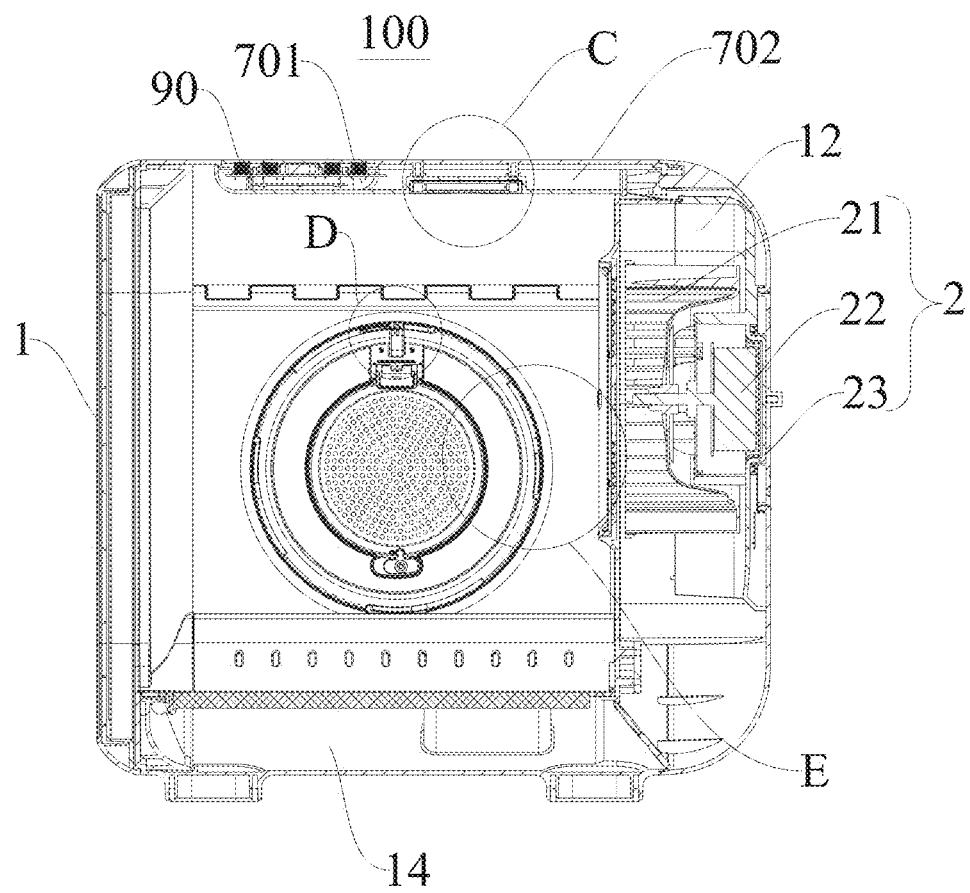
FIG. 7 is a schematic diagram of the fragrance box of the drying machine in a second configuration according to an embodiment of the present disclosure.
Figure 8:
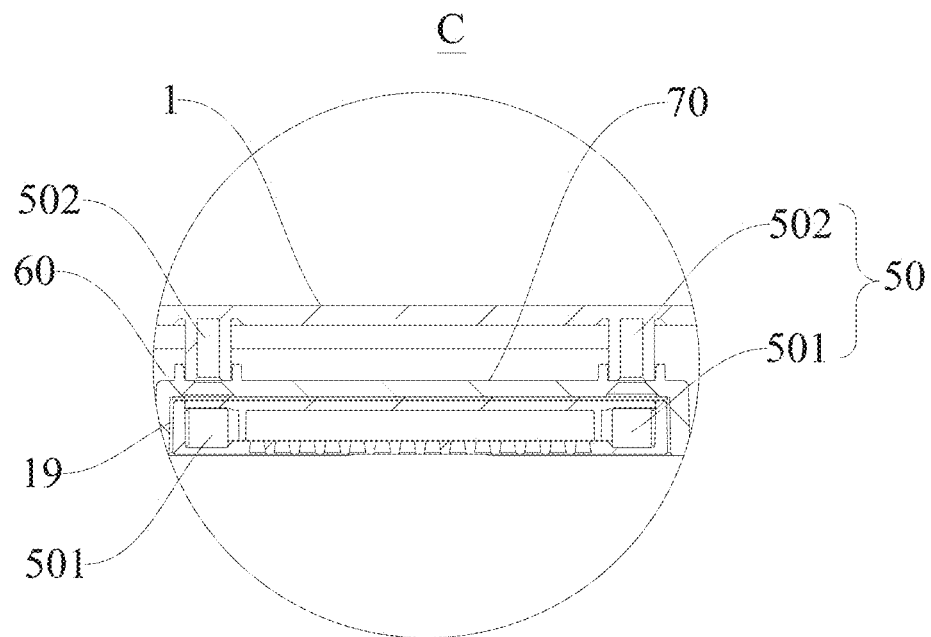
FIG. 8 is an enlarged view of part C circled in FIG. 7.

As shown in FIGS. 7 and 8, when it is required to remove the unpleasant odor in the drying machine 100 such as a pet drying machine, the fragrance box 40 may be mounted in the placement slot 19 of the box body 1, and in this case, the fragrance box 2 is brought into the second configuration, so that the fragrance box 2 can effectively diffuse a fragrance through the through holes 215 to remove the unpleasant odor in the drying machine 100, and the fragrance box 40 can be firmly fixed to the box body 1. As shown in FIGS. 5 and 6, when it is not required to remove the unpleasant odor for the drying machine 100, the fragrance box 40 may be placed in the placement slot 19 in the first configuration, in this case, the fragrance in the fragrance box 40 cannot be diffused into the box body 1, and the fragrance box 40 is stably mounted in the placement slot 19, so that the fragrance box 40 can be prevented from being shifted or lost. In addition, when the fragrance in the fragrance box 40 is not strong, the fragrance box 40 can be directly removed from the placement slot 19 and replaced with a new fragrance box 40.

According to some embodiments of the present disclosure, the through holes 4015 are formed in a side surface of the fragrance box 40. An inner wall of the placement slot 19 closes the through holes 4015 when the fragrance box 40 is in the first configuration, and the through holes 4015 are located on an open side of the placement slot 19 when the fragrance box 40 is in the second configuration. As shown in FIG. 5, the fragrance box 40 is generally in a rectangular shape, and the through holes 4015 may be formed in the upper or the lower surface of the fragrance box 40, and may also be formed in four circumferential surfaces of the fragrance box 40. When it is required to remove the unpleasant odor for the drying machine 100, a surface of the fragrance box 40 provided with the through holes 4015 may be opposite to the open side of the placement slot 19, such that the fragrance in the fragrance box 40 can be diffused into the box body 1 through the through holes 4015; and when it is not required to remove the unpleasant odor for the drying machine 100, a surface of the fragrance box 40 provided with the through holes 4015 may face away from the open side of the placement slot 19, and the inner wall of the placement slot 19 opposite to the open side may close the through holes 4015 in this case, so that the fragrance in the fragrance box 40 cannot be diffused.

In some optional embodiments, a seal 60 is provided on the inner wall of the placement slot 19, and when the fragrance box 40 is in the first configuration, the through holes 4015 are sealed by the seal 60. Referring to FIGS. 6 and 8, the seal 60 is arranged on the top wall of the placement slot 19, and the through holes 4015 are sealed by the seal 60 when the fragrance box 40 is in the first configuration. When it is not required to diffuse the fragrance from the fragrance box 40, the through holes 4015 can be sealed by the seal 60 so as to stop the diffusion of the fragrance from the fragrance box 40.

Optionally, the seal 60 is a silicone pad. However, it is not limited so. Since the silicone pad is flexible and may deform to an extent, the silicone pad can be attached to the inner wall of the placement slot 19 to seal the through holes 4015, ensuring the sealability between the seal 60 and the through holes 4015.

According to some embodiments of the present disclosure, the magnetic attraction assembly 50 comprises screws 501 and magnetic members 502, wherein the magnetic members 502 are arranged on the fragrance box 40, and the magnetic members 502 magnetically fit with the screws 501 to removably arrange the fragrance box 40 in the placement slot 19. Referring to FIGS. 5-8, the magnetic members 502 are arranged at positions on the placement slot 19 of the box body 1 corresponding to the screws 501 of the fragrance box 40. Thus, the fragrance box 40 and the box body 1 are detachably connected by means of the screws 501 and the magnetic members 502, such that the fragrance box 40 and the box body 1 are directly connected by means of a magnet effect, and no additional tool is required for dismounting, so that the fragrance box 40 is easy and quick to replace. For example, two screws 501 may be provided, the two screws 501 may be spaced apart from each other in a length direction of an upper housing 70, and the two screws 501 each are in one-to-one correspondence with two magnetic members 502, and each of the screws 501 may pass through the upper housing 70 to be threadedly connected to the inner wall of the box body 1, such that the screws 501 may securely fix the upper housing 70 to the inner wall of the box body 1 while the screws 501 magnetically fit with the magnetic members 502. In addition, when the drying machine 100 is moved, the fragrance box 40 possibly drops from the box body 1 due to the detachable connection between the fragrance box 40 and the box body 1, and the upper housing 70 provided can protect the fragrance box 40 such that the fragrance box 40 will not easily drop from the box body 1.

Figure 29:
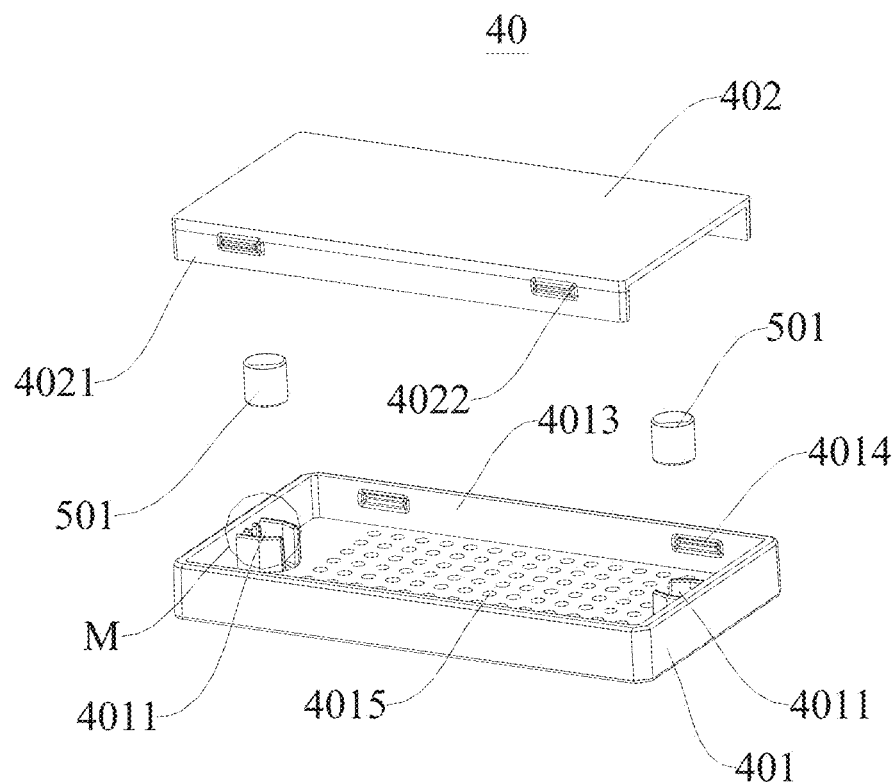
FIG. 29 is a schematic diagram of a fragrance box of the drying machine according to an embodiment of the present disclosure.

According to some specific embodiments of the present disclosure, the fragrance box 40 comprises a shell 401 and a cover 402, wherein one side of the shell 401 is open, the cover 402 is arranged on the above-mentioned side of the shell 401, the cover 402 and the shell 401 jointly define an accommodating space, the magnetic members 502 are arranged in the accommodating space, and the through holes 4015 are formed in the cover 402 and/or the shell 401. The through holes 4015 may be formed in one of the cover 402 and the shell 401, or the through holes 4015 may be formed in both the cover 402 and the shell 401. Referring to FIG. 29, one side of the shell 401 in the thickness direction is open, the cover 402 is opposite to the open side of the shell 401, and a perfume may be placed in the accommodating space to diffuse the fragrance inside the drying machine 100.

Further, as shown in FIG. 29, a plurality of through holes 4015 are provided. The plurality of through holes 4015 are formed spaced apart from each other in a surface of the bottom wall of the shell 401, and the surface of the bottom wall of the shell 401 is the lower surface of the fragrance box 40. When the shell 401 of the fragrance box 40 placed in the placement slot 19 faces the interior of the box body 1 of the drying machine 100, the fragrance of the perfume in the fragrance box 40 can be diffused into the box body 1 through the plurality of through holes 4015 to make the air inside the box body 1 more pleasant.

Further, the above-mentioned inner wall of the box body 1 and the upper housing 70 jointly define a first mounting cavity 701 and a second mounting cavity 702 that are in communication with each other, the second mounting cavity 702 is located on a side of the first mounting cavity 701 adjacent to a rear wall 13 of the box body 1, an electrical control element 90 and an electrical wire are provided in the first mounting cavity 701, one end of the electrical wire is connected to the electrical control element 90, and the other end of the electrical wire extends into the second mounting cavity 702. As shown in FIGS. 5 and 7, the fan wheel 21 of the drying machine 100 is arranged on the rear wall 13 of the box body 1, the electrical control element 90 may be arranged in an electrical control box, and the electrical control box is located in the first mounting cavity 701. One end of the electrical wire passes through the electrical control box to be connected to the electrical control element 90, and the other end of the electrical wire may passes through the second mounting cavity 702 to be connected to the electric motor 22 so as to control ON and OFF of the fan wheel 21. Thus, the space between the inner wall of the box body 1 and the upper housing 70 is fully used while the wiring of the electrical wire is facilitated, which the drying machine 100 more compact in structure.

Optionally, referring to FIGS. 5 and 7, the placement slot 19 is formed by a portion of the upper housing 70 being recessed upwardly. With such an arrangement, the placement slot 19 may be integrally formed with the upper housing 70, so that the steps of assembling the drying machine 100 can be decreased, and the assembling efficiency of the drying machine 100 can be further improved.

In some optional embodiments, third mounting recesses 4011 are formed in the shell 401, the magnetic members 502 are arranged in the third mounting recesses 4011, and the magnetic members 502 may be magnets. For example, in the example of FIG. 29, two third mounting recesses 4011 may be formed in the shell 401, and the two third mounting recesses 4011 may be respectively located at two ends in the fragrance box 40, and two magnets are provided and may be respectively mounted in the two third mounting recesses 4011. The third mounting recesses 4011 may be shaped to be adapted to the shapes of the magnets to facilitate the mounting of the magnets. Thus, the magnets can be firmly fixed to the shell 401.

Further, two protrusions 4012 spaced apart from each other are provided on the side wall of the shell 401, and the third mounting recess 4011 is defined between the two protrusions 4012. With reference to FIG. 29, the two protrusions 4012 are respectively arranged on two side walls of the shell 401 in the length direction, the two protrusions 4012 located on the same side wall are spaced apart from each other in the width direction of the shell 401, and each protrusion 4012 may extend in a direction of the cover 402, so that the two protrusions 4012 on the same side wall can limit the movement of the magnetic member 502 in the width direction of the shell 401, further ensuring the stability of the magnetic member 502 in position.

Figure 30:
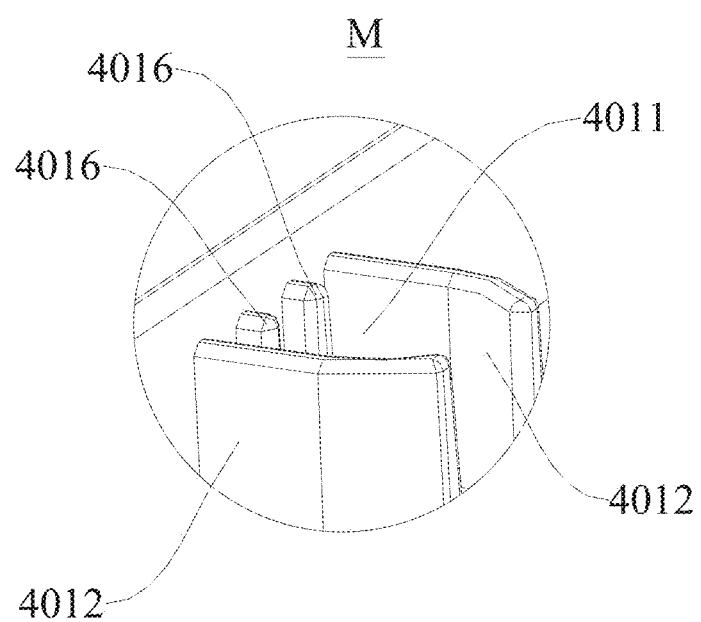
FIG. 30 is an enlarged view of part M circled in FIG. 29.

Optionally, referring to FIGS. 29 and 30, two third ribs 4016 spaced apart are provided on each of mutually opposite side surfaces of two side walls of the shell 401 in the length direction, and each third rib 4016 extends in a direction of the center of the third mounting recess 4011. Thus, the third ribs 4016 can limit the movement of the magnetic member 502 in the length direction of the shell 401, such that the magnetic member 502 is stably fixed in the third mounting recess 4011.

The magnetic members 502 are arranged inside the fragrance box 40, which is better than the case of arrangement of the magnetic members outside the fragrance box 40, so that the loss of the magnetic members 502 can be avoided. In addition, the third mounting recesses 4011 are provided in the fragrance box 40, and the magnetic members 502 can be further fixed inside the fragrance box 40, such that the fragrance box 40 can be used in combination with the box body 1 for a longer time.

According to some specific embodiments of the present disclosure, as shown in FIG. 29, the shell 401 has a shell side wall 4013, an edge of the cover 402 is provided with a cover side wall 4021 extending towards the shell 401, and the cover side wall 4021 is opposite to the shell side wall 4013. A plurality of matching protrusions 4022 are provided on one of the cover side wall 4021 and the shell side wall 4013. A plurality of matching grooves 4014 are formed in the other of the cover side wall 4021 and the shell side wall 4013, and each matching protrusion 4022 is fitted in a corresponding matching groove 4014. A plurality of matching protrusions 4022 may be provided on the cover side wall 4021, and a plurality of matching grooves 4014 (as shown in FIG. 29) may be formed in the shell side wall 4013. Alternatively, a plurality of matching grooves 4014 may be provided in the cover side wall 4021, and a plurality of matching protrusions 4022 may be provided on the shell side wall 4013 (not shown). Thus, the detachable connection of the cover 402 and the shell 401 of the fragrance box 40 can be realized, so that the user can change the perfume in the fragrance box 40 in time, improving the utilization rate of the fragrance box 40, and meanwhile, the user can also place perfume having his/her favorite fragrance between the shell 401 and the cover 402 according to his/her own preference.

Further, two cover side walls 4021 are provided, the two cover side walls 4021 are respectively arranged on two sides of the cover 402 opposite to each other, and the two cover side walls 4021 each are located in the accommodating space. Two matching protrusions 4022 spaced apart in the length direction of the cover side wall 4021 are provided on each cover side wall 4021, and the plurality of matching grooves 4014 are in one-to-one correspondence with the plurality of matching protrusions 4022. Referring to FIG. 29, the two cover side walls 4021 are respectively two side walls of the cover 402 in the width direction, and the two side walls of the shell 401 in the width direction are shell side walls 4013. Two matching grooves 4014 are provided in each shell side wall 4013, and each matching protrusion 4022 is fitted in a corresponding matching groove 4014 so as to detachably connect the cover 402 to the shell 401. By means of positioning the two cover side walls 4021 in the accommodating space, the internal space of the fragrance box 40 can be effectively utilized, and the width of the fragrance box 40 can be decreased, thereby reducing the mounting space for the fragrance box 40.

In some optional embodiments, the placement slot 19 is formed at the top of the box body 1. As shown in FIGS. 5 and 7, the fragrance box 40 is arranged in the placement slot 19 at the top of the box body 1, and the fragrance box 40 diffuses the fragrance from top to bottom at the top of the box body 1, so that the interior of the whole box body 1 can be full of the fragrance, making the air inside the box body 1 more pleasant.

In some optional embodiments, arc-shaped grooves are formed on two side walls of the placement slot 11 opposite to each other. With such an arrangement, when the fragrance box 2 is dismounted or the position of the fragrance box 2 is changed, the user can hold the fragrance box 2 through the two arc-shaped grooves and remove the fragrance box 2 from the placement slot 11 to complete the dismounting or position change of the fragrance box 2.

According to some embodiments of the present disclosure, the placement slot 19 is formed in the rear of the box body 1. With reference to FIGS. 1, 5 and 7, since the fan wheel 21 of the drying machine 100 is arranged in the rear of the box body 1, when the drying machine 100 is used for drying the pet, the pet easily moves in the front of the box body 1 by means of positioning the placement slot 19 closer to the rear wall 13 of the box body 1, so that the pet can be prevented from damaging the fragrance box 40, thereby prolonging the service life of the fragrance box 40.

Optionally, an perfume may be provided in the fragrance box 40 in advance, so that the user can directly use the fragrance box 40 without manually filling an perfume during use.

According to some embodiments of the present disclosure, a front side of the box body 1 is open, and the front side of the box body 1 is provided with the door body 8 for opening or closing the above-mentioned front side of the box body 1. For example, in the examples of FIGS. 1 and 4, when the door body 8 is opened, the pet can be placed into the box body 1 or removed from the box body 1 through the door body 8. When the pet is to be positioned inside the box body 1 for drying, the door body 8 is opened, the pet can enter the box body 1 through the door body 8, the door body 8 is then closed, and the fur of the pet is dried in the box body 1 to realize the drying function of the drying machine 100. After the cat stroking door 172 on the viewing window 10 is removed, the pet such as a cat can freely enter or exit the box body 1 through the cat stroking opening 171, and the box body 1 has good ventilation and air permeability, so the pet such as the cat can sleep and play in the box body 1 to realize the function of a cat nest. Normally, one pet is dried by the drying machine 100 about once every half a month, and the function of the cat nest is added for the drying machine 100 while the drying function is realized, thereby greatly improving the practicability and utilization rate of the drying machine 100.

Optionally, multi-stage temperature control and measurement may be provided inside the box body 1 to prevent the discomfort of the pet in the box body 1 due to excess temperature in the box body 1.

Optionally, an illuminator may be provided inside the box body 1, such as a LED intelligent lamp, to facilitate mounting or dismounting of the second partition plate 3 in the box body 1 and to facilitate cleaning of the box body 1.

Other configurations, etc. and operations of the drying machine 100 according to embodiments of the present disclosure are known to those of ordinary skill in the art and will not be described in detail herein.

In the description, the explanation with reference to the terms such as "an embodiment", "some embodiments", "exemplary embodiments", "an example", "specific examples", or "some examples" means that specific features, structures, materials, or characteristics described in combination with the embodiment(s) or example(s) are included in at least one embodiment or example of the disclosure. In the description, the illustrative expressions of the above-mentioned terms are not necessarily referring to the same embodiment or example. Moreover, the specific features, structures, materials, or characteristics described herein may be combined in any one or more embodiments or examples in a suitable manner.

Although the embodiments of the present disclosure have been shown and described, those of ordinary skill in the art can understand that various changes, modifications, substitutions, and variations can be made to these embodiments without departing from the principles and spirit of the present disclosure. The scope of the present disclosure is defined by the claims and equivalents thereof.

The invention claimed is:

1. A drying machine comprising:
 a box body, wherein a first partition plate is provided in the box body, the first partition plate is located in front of a rear wall of the box body, and a drying cavity and a first accommodation cavity are respectively located on two sides of the first partition plate, the first accommodation cavity is defined between the first partition plate and the rear wall, a fan wheel is provided in the first accommodation cavity, and a rotation axis of the fan wheel is perpendicular to the first partition plate and the rear wall, a first air inlet is formed in the first partition plate, and a second air inlet is formed in the rear wall;
 when the fan wheel rotates, an airflow inside the drying cavity is suitable for entering the first accommodation cavity through the first air inlet under the action of the fan wheel and then flowing into the drying cavity, and an airflow outside the drying machine is suitable for entering the first accommodation cavity through the second air inlet under the action of the fan wheel and then flowing into the drying cavity to realize the inner circulation and the outer circulation of air by means of one fan wheel,
 wherein each of the first air inlet and the second air inlet is axially opposite to the fan wheel, a virtual straight line where the rotation axis of the fan wheel is located passes through the first air inlet and the second air inlet, the fan wheel is located between the first air inlet and the second air inlet, an orthographic projection of the fan wheel on the first partition plate overlaps the first air inlet, and an orthographic projection of the fan wheel on the rear wall overlaps the second air inlet.

2. The drying machine according to claim 1, further comprising a fan wheel housing provided between the first partition plate and the rear wall, wherein the fan wheel is arranged in the fan wheel housing, and an air channel is defined between the fan wheel and the fan wheel housing, the fan wheel comprises an air inlet channel located at an inner side of the air channel in a radial direction of the fan wheel, the first air inlet and the second air inlet are directly communicated with the air inlet channel, and
 when the fan wheel rotates, the airflow in the drying cavity sequentially flows through the first air inlet and the air channel and then flows into the drying cavity, and the airflow outside the drying machine sequentially flows through the second air inlet and the air channel and then flows into the drying cavity.

3. The drying machine according to claim 2, further comprising a second partition plate provided in the box body, wherein a second accommodation cavity in direct communication with an air channel outlet of the air channel is defined between the second partition plate and an inner wall of the box body at a position in the fan wheel housing corresponding to the air channel outlet, an air outlet is formed in the second partition plate, and the drying cavity is located above the second partition plate; and when the fan wheel operates to rotate, the airflow inside the drying cavity is suitable for sequentially flowing through the first air inlet, the air channel, the second accommodation cavity and flowing into the drying cavity through the air outlet, and the airflow outside the drying machine is suitable for sequentially flowing through the second air inlet, the air channel, the second accommodation cavity and flowing into the drying cavity through the air outlet.

4. The drying machine according to claim 3, wherein the second partition plate is removably arranged in a lower portion of the box body.

5. The drying machine according to claim 3, wherein the air outlet comprises a plurality of air outlet orifices; and
the second partition plate comprises:
a partition plate body; and
two partition plate sections, wherein the two partition plate sections are respectively arranged on the left side and the right side of the partition plate body, the two partition plate sections extend obliquely upwards from bottom to top in a direction away from the center of the partition plate body, and a plurality of air outlet orifices are formed in both the two partition plate sections and the partition plate body.

6. The drying machine according to claim 5, wherein each partition plate section is an arc-shaped partition plate projecting away from the partition plate body.

7. The drying machine according to claim 2, further comprising a heating assembly provided at an air outlet of the air channel.

8. The drying machine according to claim 7, further comprising a negative ion generator provided on the first partition plate, wherein an output end of the negative ion generator extends into the first accommodation cavity; and
an ozone disinfection apparatus is provided on the heating assembly.

9. The drying machine according to claim 2, wherein the air channel is a spiral air channel.

10. The drying machine according to claim 2, wherein the air channel has an air channel outlet, and the cross-sectional area of at least a portion of the air channel gradually increases toward the air channel outlet in a circumferential direction of the fan wheel.

11. The drying machine according to claim 2, wherein the fan wheel housing is arranged on at least one of the first partition plate and the rear wall.

12. The drying machine according to claim 11, wherein the drying machine further comprises an electric motor support; and
the fan wheel housing comprises:
a first fan wheel housing arranged on the first partition plate; and
a second fan wheel housing arranged on the electric motor support, the second fan wheel housing and the first fan wheel housing jointly defining a fan wheel accommodation cavity for accommodating the fan wheel.

13. The drying machine according to claim 12, wherein the electric motor support is formed with an air inlet hole that runs therethrough in an axial direction of the fan wheel, the electric motor support is in sealed connection with the rear wall on a peripheral side of the air inlet hole, and outside air sucked by the fan wheel sequentially passes through the second air inlet and the air inlet hole and enters the fan wheel accommodation cavity.

14. The drying machine according to claim 12, wherein the electric motor support is detachably connected to the first partition plate.

15. The drying machine according to claim 12, further comprising an electric motor provided in the fan wheel accommodation cavity and an output shaft of the electric motor fixed to the fan wheel, wherein the electric motor is mounted on the second fan wheel housing.

16. The drying machine according to claim 1, wherein the fan wheel is a forward-inclined fan wheel.

17. The drying machine according to claim 1, further comprising at least one cat stroking opening formed in the box body, and a cat stroking door provided at the cat stroking opening for opening or closing the cat stroking opening.

18. The drying machine according to claim 17, further comprising an opening formed in the box body and a removable viewing window provided at the opening, wherein the cat stroking opening is formed in the viewing window.

19. The drying machine according to claim 18, wherein one end of the cat stroking door is pivotably connected to the viewing window by means of a pivoting assembly; and
a locking assembly is provided between the other end of the cat stroking door and the viewing window, the cat stroking door is adapted for opening the cat stroking opening when the locking assembly is unlocked, and the cat stroking door is fixed to the viewing window when the other end of the cat stroking door is locked by the locking assembly.

20. The drying machine according to claim 1, further comprising a placement slot formed in the box body and a fragrance box removably arranged in the placement slot by means of a magnetic attraction assembly, wherein the fragrance box has a first configuration and a second configuration in the placement slot, at least one through hole is formed in the fragrance box, the interior of the fragrance box is not in communication with the interior of the box body when the fragrance box is in the first configuration, and the interior of the fragrance box is in communication with the interior of the box body through the through hole when the fragrance box is in the second configuration.

* * * * *